United States Patent
Nordbo et al.

(10) Patent No.: US 11,786,409 B2
(45) Date of Patent: Oct. 17, 2023

(54) WOUND PADS

(71) Applicant: Mölnlycke Health Care AB, Gothenburg (SE)

(72) Inventors: Kalle Jon Nordbo, Roskilde (DK); Jerker Gröndahl, Västra Frölunda (SE); Esbjörn Olsson, Mölndal (SE); Bengt Olof Sebastian Engwall, Malmö (SE)

(73) Assignee: Mölnlycke Health Care AB, Gothenburg (SE)

( * ) Notice: Subject to any disclaimer, the term of this patent is extended or adjusted under 35 U.S.C. 154(b) by 419 days.

(21) Appl. No.: 14/899,279

(22) PCT Filed: Mar. 31, 2014

(86) PCT No.: PCT/EP2014/056453
§ 371 (c)(1),
(2) Date: Dec. 17, 2015

(87) PCT Pub. No.: WO2015/000610
PCT Pub. Date: Jan. 8, 2015

(65) Prior Publication Data
US 2016/0206478 A1  Jul. 21, 2016

(30) Foreign Application Priority Data
Jul. 5, 2013  (EP) .................................... 13175220

(51) Int. Cl.
*A61F 13/00* (2006.01)
*A61F 15/00* (2006.01)
*A61M 1/00* (2006.01)

(52) U.S. Cl.
CPC .. *A61F 13/00068* (2013.01); *A61F 13/00021* (2013.01); *A61F 13/00085* (2013.01);
(Continued)

(58) Field of Classification Search
CPC ................ A61F 13/00021; A61F 13/00; A61F 13/00004; A61F 13/00068; A61F 13/20;
(Continued)

(56) References Cited

U.S. PATENT DOCUMENTS

| | | | | |
|---|---|---|---|---|
| 4,699,134 A | * | 10/1987 | Samuelsen | A61F 13/0223 602/56 |
| 2009/0181074 A1 | * | 7/2009 | Makower | A61F 13/00017 424/447 |

(Continued)

FOREIGN PATENT DOCUMENTS

| | | |
|---|---|---|
| EP | 0164319 A2 | 12/1985 |
| WO | WO-2010/092334 A2 | 1/2010 |

(Continued)

OTHER PUBLICATIONS

Dictionary.com, "unit," https://www.dictionary.com/browse/unit.*
(Continued)

*Primary Examiner* — Victoria Hicks Fisher
(74) *Attorney, Agent, or Firm* — Ballard Spahr LLP

(57) ABSTRACT

Described are wound pads for use, e.g., as cavity wound fillers, having shapes with rounded corners, the projection on an X-Y plane of at least one corner having a curvature distinct from that of the projection of the other corners. Negative pressure systems and kits that includes such wound pads, and methods of using such wound pads are also described.

16 Claims, 12 Drawing Sheets

(52) U.S. Cl.
CPC ............ *A61F 15/001* (2013.01); *A61M 1/915* (2021.05); *A61F 2013/00174* (2013.01); *A61F 2013/00357* (2013.01); *A61F 2013/00812* (2013.01); *A61F 2013/00842* (2013.01)

(58) Field of Classification Search
CPC ...... A61F 13/00085; A61F 2013/00089; A61F 2013/00106; A61F 2013/00174; A61F 2013/00361; A61F 2013/00357; A61F 2013/00812; A61F 2013/008; A61F 2013/00795; A61F 13/02; A61F 13/04; A61F 2013/00842; A61F 2013/00553; A61F 2013/00557; A61F 2013/00544; A61F 13/00051; A61F 13/15; A61F 13/45; A61F 13/474; A61F 13/505; A61F 15/008; A61F 13/0223; A61F 2013/530802; A61F 2013/00863; A61F 2013/00855; A61F 2013/0074; A61F 2007/0212; A61F 13/2057; A61F 2013/5113; A61F 2013/51134; A61F 2013/530649; A61F 2013/530656; A61F 2013/53081; A61F 2013/530817; A61F 13/00034; A61F 13/00042; A61F 13/00046; A61F 2013/00217; A61L 15/425
USPC ........................................................ D24/189
See application file for complete search history.

(56) References Cited

U.S. PATENT DOCUMENTS

2009/0227969 A1   9/2009  Jaeb et al.
2011/0213287 A1*  9/2011  Lattimore ......... A61F 13/00021
                                                             602/46
2012/0041403 A1   2/2012  Bennett et al.

FOREIGN PATENT DOCUMENTS

WO    WO-2011/106722 A1    9/2011
WO    WO-2014/014871 A1    1/2014
WO    WO-2015/061352 A2    4/2015
WO    WO-2015/061352 A3    9/2015

OTHER PUBLICATIONS

Dictionary.com, "unitary," https://www.dictionary.com/browse/unitary.*

Dictionary.com, "along," https://www.dictionary.com/browse/along.*

International Search Report dated Jul. 8, 2014 by the International Searching Authority for application PCT/EP2014/056453, filed on Mar. 31, 2014, and published as WO 2015/000610 on Jul. 8, 2015 (Applicant—Mölnlycke Health Care AB // Inventor—Nordbo, et al.) (4 pages).

\* cited by examiner

WOUND PADS

CROSS-REFERENCE TO RELATED APPLICATIONS

This application is a U.S. National Phase Application of International Application No. PCT/EP2014/056453, filed Mar. 31, 2014, which claims priority to European Patent Application No. 13175220.6, filed Jul. 5, 2013, each of which are hereby incorporated by reference in their entirety.

TECHNICAL FIELD

The present invention relates to a wound pad having a shape with corners and to a system for treating wounds using negative pressure, the system comprising such a wound pad. The present invention also relates to a kit for negative pressure therapy, comprising such a wound pad, and to a method.

BACKGROUND

Some wounds, such as pressure or diabetic ulcer wounds, or surgically created wounds, form a cavity in a patient's body. It can be desirable to fill the wound cavity, e.g., as part of a course of treatment. Various types of wound dressings or pads are used to fill wound cavities. These wound dressings or pads must be fitted for the particular wound size and shape, which can vary greatly. Some such dressings are easily conformable to the size and shape of the particular wound being treated. For example, gauze may be used as a cavity wound filler. As a further example, MELGISORB™ (produced by Mölnlycke Health Care) is a soft, sterile calcium sodium alginate dressing that is used to pack wound cavities.

In some wound care contexts, it can be desirable to use a wound pad made of a less conformable material. For example, porous and semi-rigid polymer foams are often used as wound fillers during negative pressure wound treatment. These materials may offer the advantage of allowing fluid channels through themselves even when subjected to negative pressure. Without wishing to be bound by any particular theory, it is also thought that the mechanical interaction between these more rigid materials and the wound may contribute to wound healing processes.

The suitability of such less conformable materials notwithstanding, these dressings or pads can be difficult to size and shape to fit a wound. Such pads are typically supplied in one of several standard sizes and shapes, which then must be individually altered, typically with a utensil such as scissors. The process of individually shaping and sizing a wound pad can be messy, time-consuming, and/or frustrating to the clinician and/or patient.

SUMMARY

The present invention encompasses the recognition that articles that are wound pads that can easily be shaped and sized, even if the material is somewhat rigid, would be particularly advantageous in wound care contexts.

In one aspect, the present invention provides a wound pad for application in a wound. The wound pad has a main extension parallel to an X-Y plane of a Cartesian coordinate system with axes X, Y and Z, and a thickness in the Z direction of said Cartesian coordinate system. The wound pad has a plurality of corners, each corner being at least one of 1) provided as a rounded corner, the projection of which on the X-Y plane has a curvature, or 2) removable, by manually separating a corner piece of the wound pad delineated by a corner incomplete cut so as to leave a rounded corner, the projection of which on the X-Y plane has a curvature. The projection on the X-Y plane of at least one rounded corner has a curvature which differs from the curvature of the projection on the X-Y plane of any of the other corners.

The wound pad may be a one-piece wound pad. Any portion of the one-piece wound pad may be adapted for application in a wound. That is to say, the entire wound pad, including the corner pieces are suitable for being in contact with a wound. Thus, the wound pad is, for instance, suitable for use as a wound filler. Of course, the wound pad can be used as one part of a system comprising other parts which are not meant to be applied in a wound, for example an adhesive wound cover adapted to be attached to the skin surrounding a wound.

One way of determining the curvature of the projection on the X-Y plane of a rounded corner may be to measure the respective radii of circular arcs which best approximate the projection at each point. Every such circular arc is parallel with the X-Y plane. The curvature at a specific point on the projection is the reciprocal of the corresponding radius, and the curvature of a projection may be defined as the set of curvatures at all such specific points. Thus, when the projection on the X-Y plane of at least one rounded corner (e.g. a first rounded corner) has a curvature which differs from the curvature of the projections on the X-Y plane of any of the other corners (e.g. second rounded corners), this may in some embodiments be presented as the curvature of the entire projection of the first rounded corner being different from the entire projections of the second rounded corners. In some embodiments only sections of the projection on the X-Y plane of the first rounded corner differs from the projection of any one of or each one of the projections of the second rounded corners.

Many embodiments of the wound pad are conceivable. For example, in some embodiments all corners may be provided as rounded corners. In some embodiments, the curvatures of at least two projections may differ from the curvature of the other projections. In some embodiments, the curvatures of said at least two projections may differ from each other. In some embodiments, the curvatures of all projections may differ from each other.

Furthermore, in some embodiments at least one projection may have a constant curvature. In some embodiments, all such constant curvatures are different from each other. In other embodiments, some constant curvatures are the same. For instance, with reference to the above example with the first rounded corner and second rounded corners, the projection on the X-Y plane of the first rounded corner may in some embodiment have a constant curvature which may be defined as $1/r_1$, wherein $r_1$ is the radius of a circular arc defining the projection of the first rounded corner. The projection of one of the second rounded corners may be defined as $1/r_2$, wherein $r_2$ is the radius of a circular arc defining the projection of the second rounded corner, and wherein $r_1$ is different from $r_2$.

In general terms, if the projection of each one of the rounded corners has a constant curvature it may in general terms be expressed as for each projection of a rounded corner i (i=1, 2, 3 . . . n) the curvature is $1/r_i$. In some embodiments at least $r_1$ is different from at least one of the other radii $r_i$, while in some embodiments $r_1$ is different from at least two or even different from all other radii $r_i$. In some embodiments at least $r_1$ and $r_2$ are different from at least one of the other radii $r_i$. In some embodiments each one of the radii $r_i$ is different from any other of the radii $r_i$.

In some embodiments the corner incomplete cut may extend from a first edge portion of the wound pad to a second edge portion of the wound pad, each perimeter edge portion connecting two neighbouring corners, wherein said first edge portion of the wound pad connects a common corner with a first neighbouring corner and said second edge portion connects said common corner with a second neighbouring corner. In some embodiments the edge portions may be straight.

In some embodiments the corner incomplete cut may extend from a first perimeter edge of the wound pad to a second perimeter edge of the wound pad, each outer perimeter edge portion connecting two neighbouring corners, wherein said first perimeter edge of the wound pad connects a common corner with a first neighbouring corner and said second perimeter edge connects said common corner with a second neighbouring corner. In some embodiments the perimeter edges may be straight.

In some embodiments the wound pad may have four corners and two pairs of opposite perimeter edges, the perimeter edges of each pair being substantially parallel with each other and substantially perpendicular to the straight portions of the other pair. The four corners (a first corner, a second corner, a third corner, and fourth corner) and the four perimeter edges (a first perimeter edge, a second perimeter edge, a third perimeter edge, and a fourth perimeter edge) together define the shape and perimeter edge of the wound pad.

Hence, in certain embodiments, provided wound pads have a substantially planar rectangular shape with four rounded corners, wherein the thickness of the wound pad is less than the width and less than the length of the wound pad. In some embodiments, provided wound pads comprise at least one main incomplete cut extending through at least a portion of the thickness of the pad, wherein the at least one main incomplete cut delineates at least two sections of the wound pad that can be manually separated from each other, and wherein the wound pad is structurally intact. In some embodiments, provided wound pads comprise an open-cell foam, e.g., a polymer foam.

In one aspect, the present invention provides systems for the treatment of wounds using negative pressure, such systems comprising a negative pressure source for providing negative pressure to a wound, a wound pad in accordance with certain embodiments of the invention, a wound cover disposed over the wound pad, and a conduit configured to transmit negative pressure from the negative pressure source to the wound cover.

In one aspect, the present invention provides kits for negative pressure wound therapy, comprising a wound pad according to certain embodiments of the invention and at least one item selected from the group consisting of: a wound contact layer, a wound cover, and a wound interface device.

In one aspect, the present invention provides methods comprising the steps of: providing a wound pad in accordance to any embodiments of the invention, choosing one of the rounded corners of the wound pad based on the suitability of the rounded corner's curvature with the size and shape of at least part of the wound, placing the chosen corner into the wound, and fitting the rest of the wound pad into the wound.

BRIEF DESCRIPTION OF THE DRAWING

FIGS. 1a-8b show perspective and top views, respectively, of exemplary wound pads of the invention that are substantially planar (FIGS. 1a, 2a, 3a, etc. show perspective views while FIGS. 1b, 2b, 3b, etc. show the corresponding top views). In FIGS. 1a-7b, each corner has a distinct curvature from all other corners. FIGS. 8a-8b show an embodiment in which a wound pad is provided with corner incomplete cuts near the corners that, when used to remove the corner piece or piece(s), would leave behind a corner that has a distinct curvature as compared to the other corners that would be left behind when the corresponding corner pieces are removed. Embodiments shown in FIGS. 2a-9 and 12 include main incomplete cuts that can be used to shape and size the wound pad, which may be provided in a similar manner as said corner incomplete cuts for removing a corner piece. However, while the corner incomplete cuts delineate a corner piece, the main incomplete cuts will generally have a longer extension, for instance, from one edge of the wound pad to an opposite edge thereof.

FIGS. 8a-8b show an embodiment in which a wound pad is provided with corner incomplete cuts 6a, 8a, 10a, 12a (indicated in FIG. 8b) near the corners that, when used to remove the corner piece or piece(s), would leave behind a corner that has a distinct curvature as compared to the other corners that would be left behind when the corresponding corner pieces are removed. Corner piece 6 is the smallest corner piece and is delineated by the shortest corner incomplete cut 6a, and corner piece 12, delineated by the longest corner incomplete cut is 12a, is the largest corner piece. Corner pieces 8 and 10, delineated by corner incomplete cuts 8a and 10a, respectively, present two different medium sized corner pieces. The wound pad of FIGS. 8a and 8b is also provided with two main incomplete cuts 40 and 42. Main incomplete cut 40 extends from one edge of the wound pad to an opposite edge of the wound pad, while main incomplete cut 42 extends from one edge of the wound pad to a neighbouring edge of the wound pad. Each main incomplete cut 42 allows a section to be manually separated from the rest of the wound pad. Such sections are larger than any corner piece that may be separated. For instance, each section which is delineated by a main incomplete cut and which is thereby separable from other sections of the wound pad has a volume greater than 5% of the total volume of the wound pad before the separation of any sections. Suitably, a section delineated by a main incomplete cut has a volume greater than 10%, and in some embodiments greater than 15%, or greater than 20% of the total volume of the wound pad.

DEFINITIONS

Figure 1A:
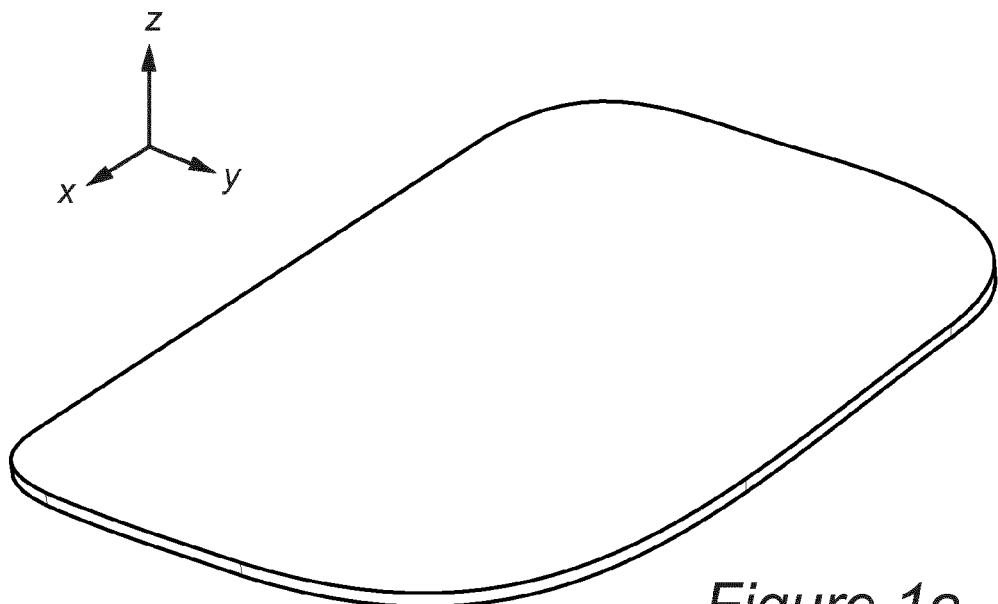
Figure 1B:
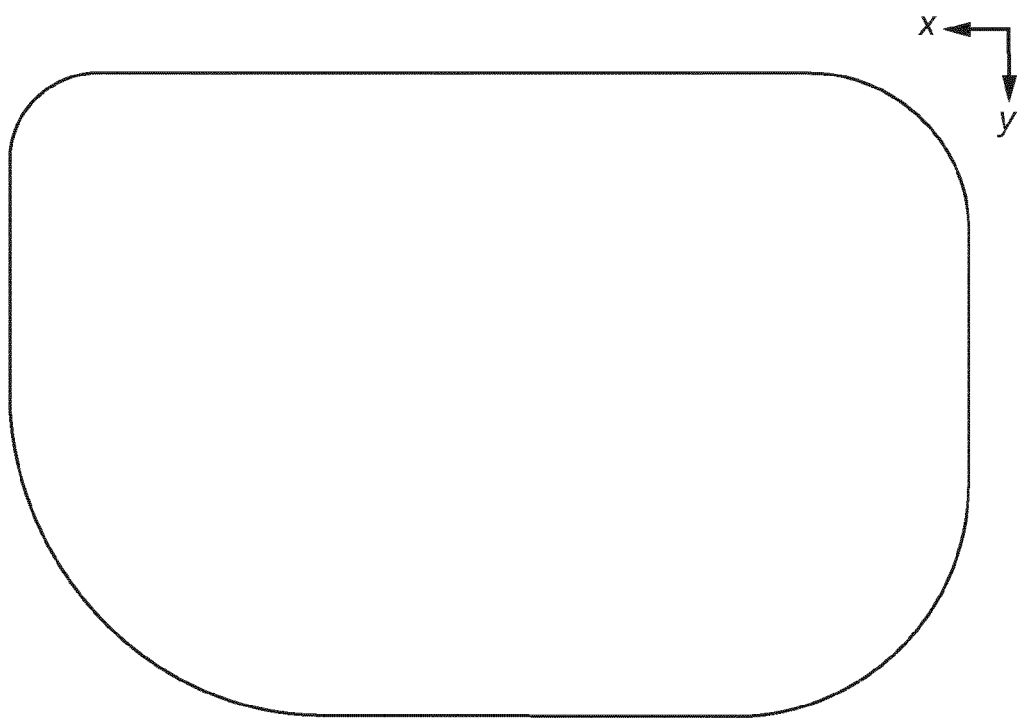

As used herein, the term "arcuate" refers to a shape that is curved like a bow. The term encompasses at least arc shapes that are obtained from part of a circle or an ellipse.

As used herein, the term "connection region" refers to a region within an incomplete cut where two or more sections of an object, e.g., a wound pad, are connected, for example, by not having been cut at all, by not having been cut completely, by joining of two formerly separated pieces, etc.

As used herein, the term "corner piece" refers to a part of an object, e.g., a wound pad, that is present at a corner of the object, made of the same material as the rest of the object, and whose removal leaves a corner that is convex with respect to the object that remains after removal (e.g., the curve is "outward" with respect to the body of the object remaining after removal of the corner piece). Furthermore, the corner piece has a volume no greater than 5% of the total volume of the object before the removal of any corner piece(s). In some embodiments, the corner piece has a volume no greater than 3% of the total volume of the object before the removal of any corner piece(s). In some embodiments, the corner piece has a volume no greater than 2% of the total volume of the object before the removal of any corner piece(s). In some embodiments, the corner piece has a volume no greater than 1% of the total volume of the object before the removal of any corner piece(s). In some embodiments, the corner piece is manually separable from the rest of the wound pad. In some such embodiments, removal of the corner piece leaves a corner that has a different contour (e.g., shape and/or curvature) than the contour of the corner before removal of the corner piece. For example, in some embodiments, one or more corners of a wound pad have incomplete cuts near the corners ("corner incomplete cut" as further described herein) that can be used to manually separate corner pieces from the rest of the wound pad, and removal of such corner pieces leave a rounded corner having a curvature in one plane of the wound pad, e.g. the X-Y plane of a substantially planar wound pad whose thickness is in the Z direction. Non-limiting examples of corner pieces are depicted as shown by reference numbers 6, 8, 10, and 12 in FIG. 8*b*.

As used herein, the term "curvature" refers to properties of a curve that include the general shape and radius or radii of the curve. For example, curves that are circular arcs ("circular curves") may be described at least partly by the radius of the circle from which the arc is obtained ("radius of curvature"). Such curves may also be described by the angle that is subtended by the circular arc (i.e., 180 degrees corresponds with a half-circle and 90 degrees corresponds with a quarter-circle.) It should be understood that not all curves included in the scope of the present application are necessarily circular arcs. As a non-limiting example, curves that are arcs from an ellipse ("elliptical curves") are also contemplated. Such curves may be described by, among other things, the radii of the major and minor axes of the ellipse. Elliptical curves can also be described, for example, by a starting and end angle from an ellipse as measured from the center or one of the foci of the ellipse in relation to a reference axis such as the major axis.

Curves that have different curvatures may differ in one or more properties of a curve. For example, two curves may have the same shape but nonetheless differ in curvature because they have different radii of curvature.

Figure 4A:
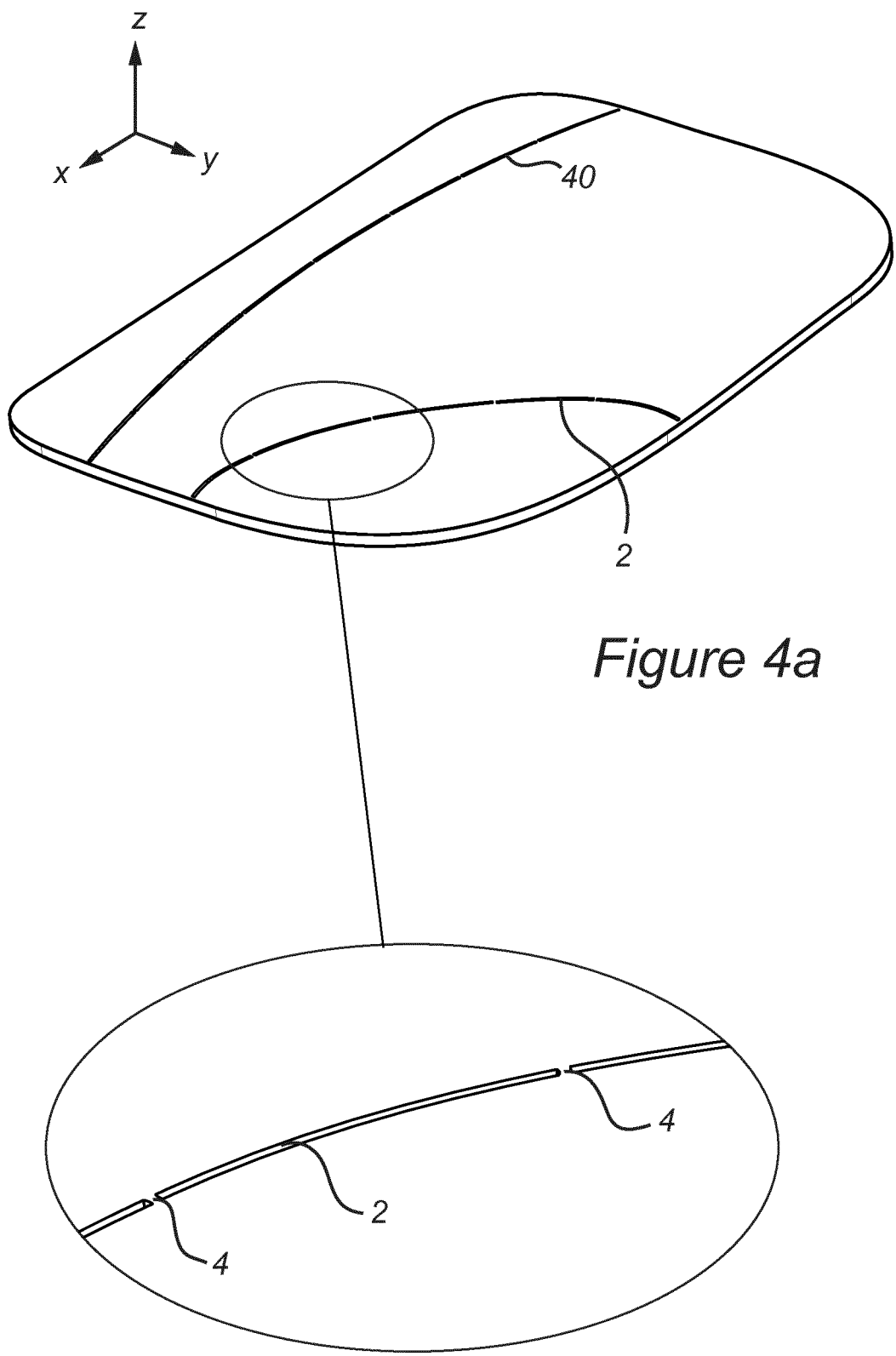
Figure 4B:
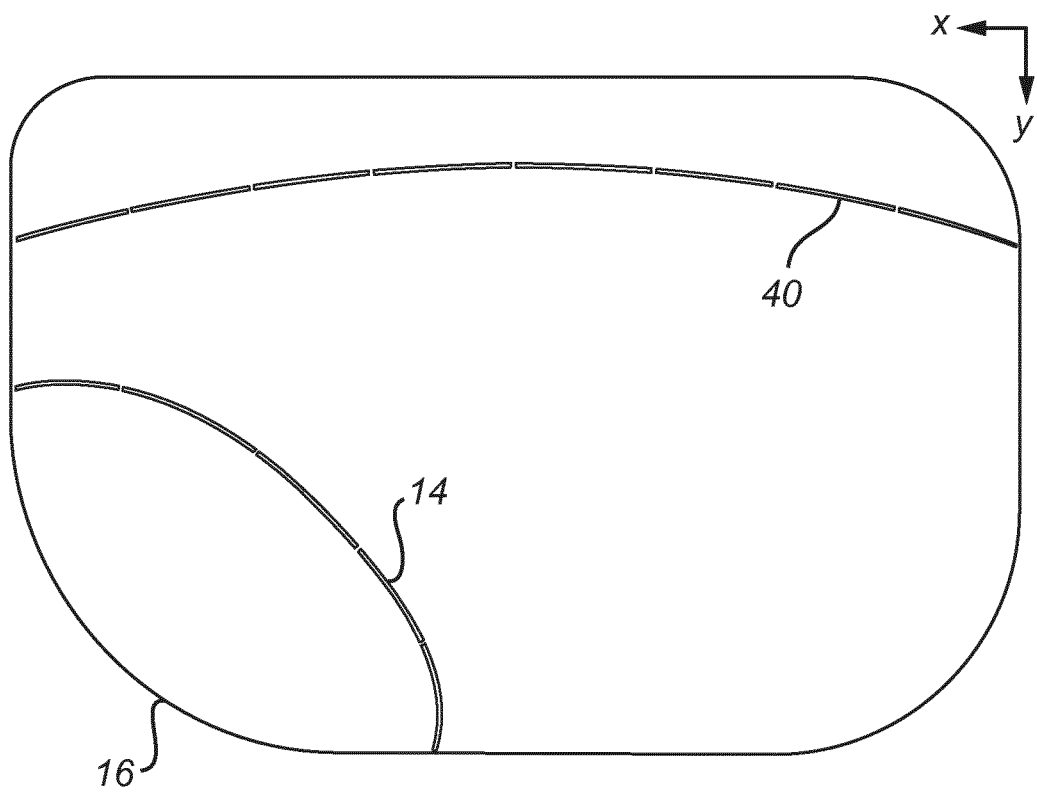
Figure 5A:
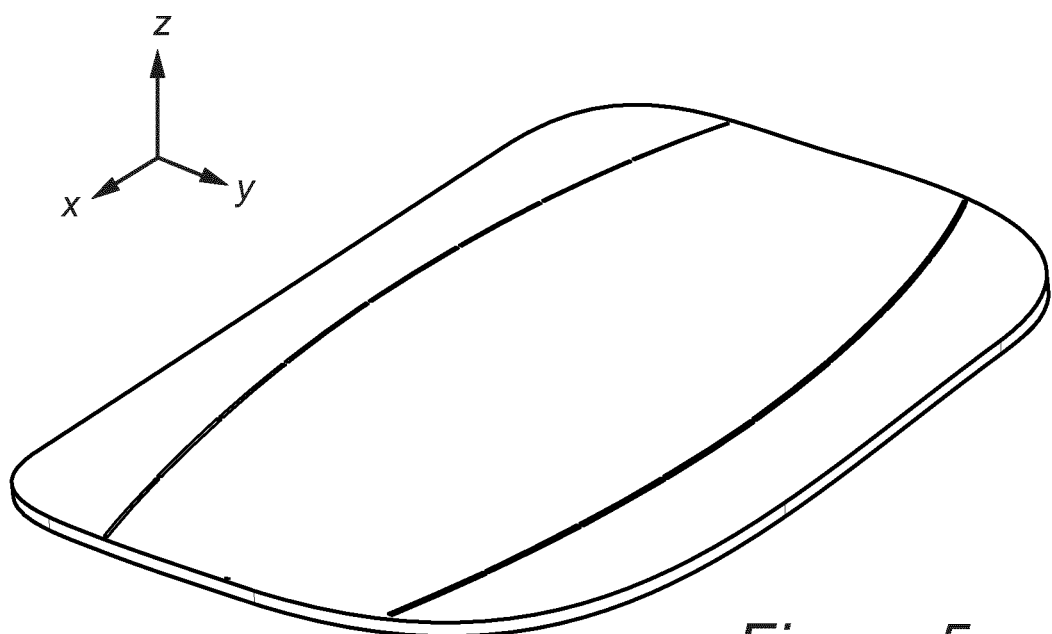
Figure 5B:
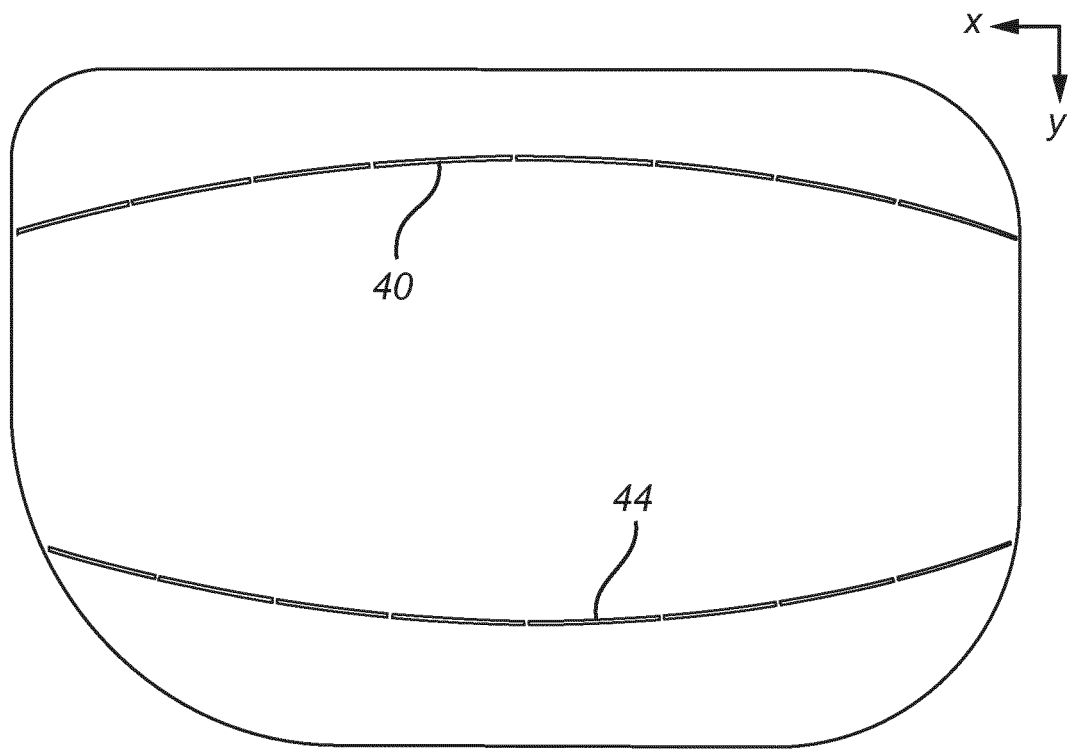
Figure 6A:
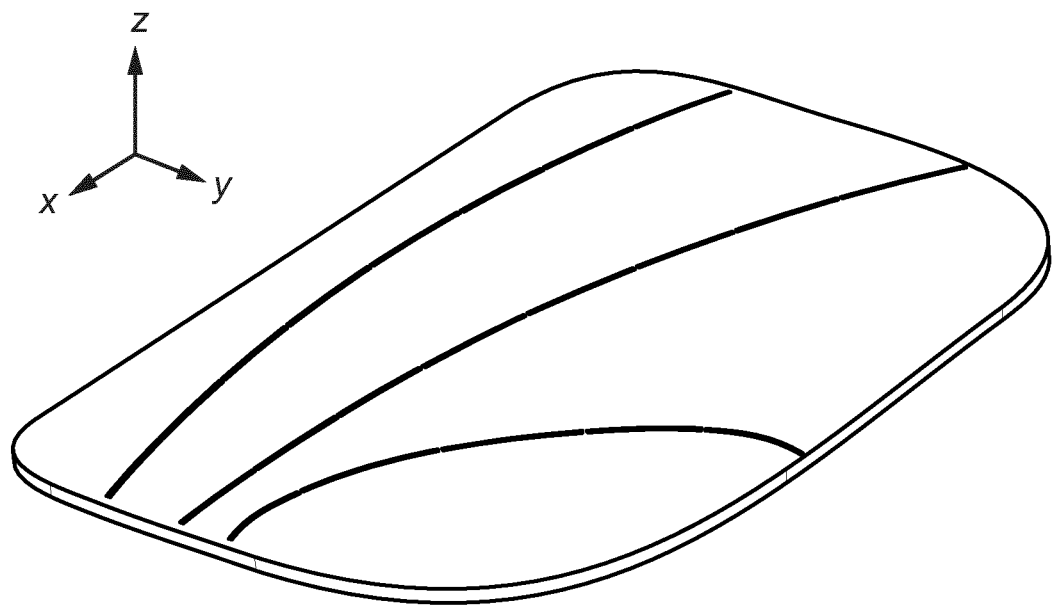
Figure 6B:
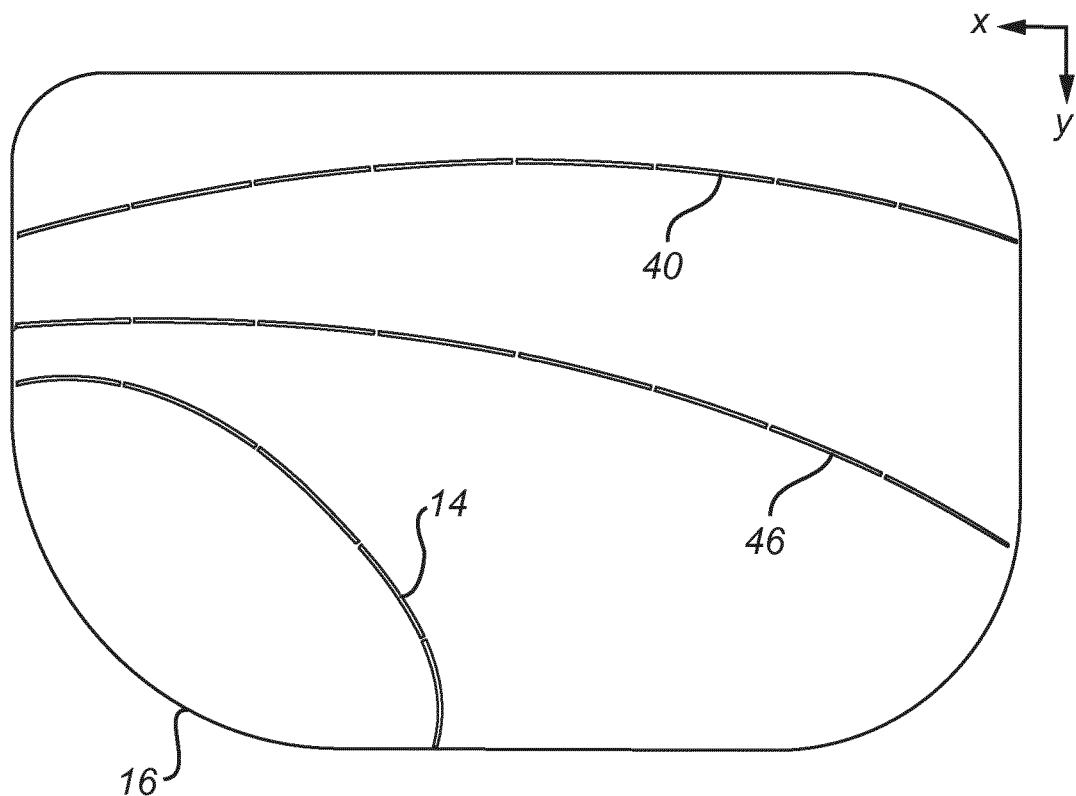
Figure 7A:
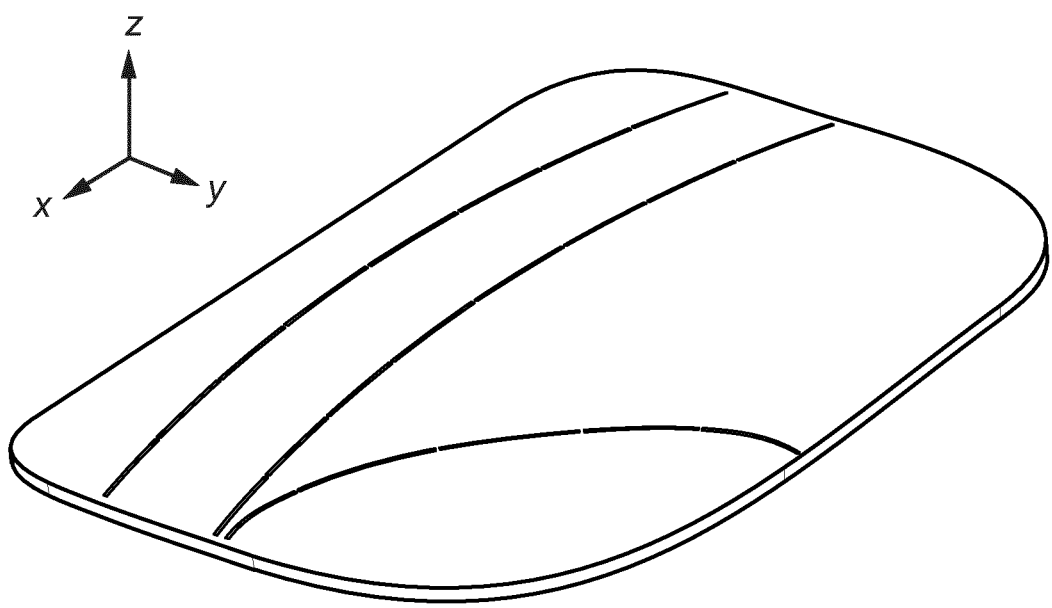
Figure 7B:
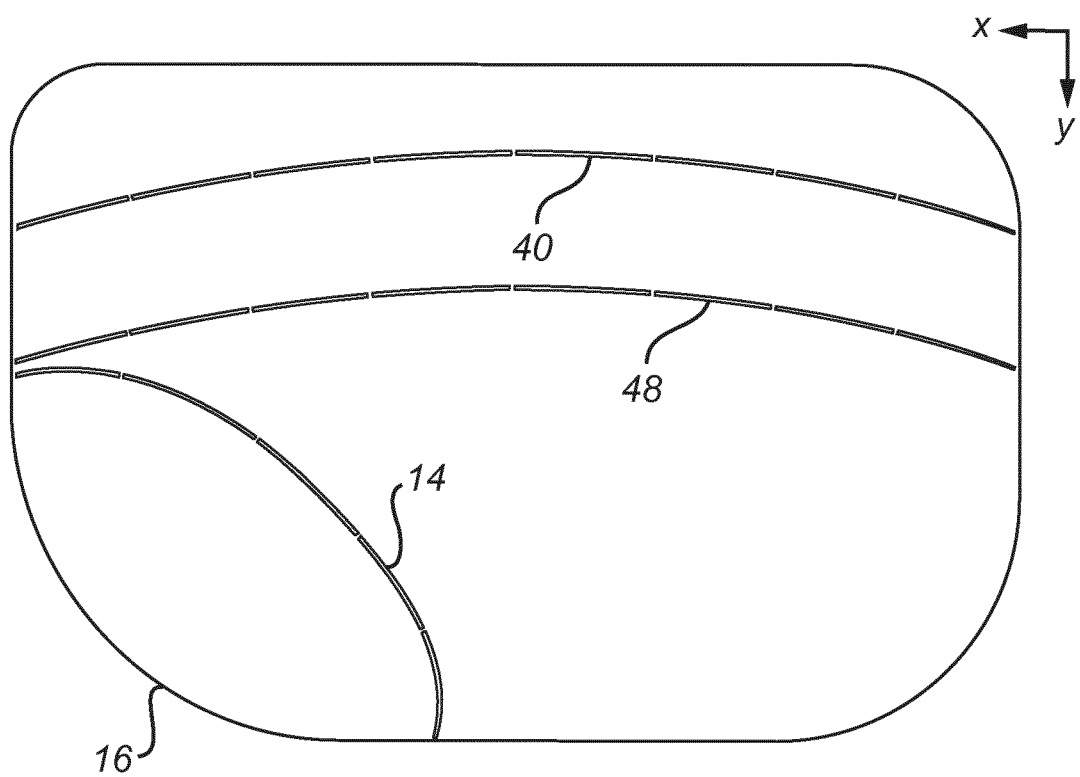

As used herein, the term "incomplete cut" refers to a feature of an object, e.g., a wound pad, that delineates at least two sections of the object that can be manually separated from one another, while allowing the object to remain structurally intact unless and until the sections are manually separated from one another. In some embodiments, an incomplete cut comprises a cut with one or more connection regions. In some embodiments, an incomplete cut comprises a perforation. In some embodiments, an incomplete cut comprises both a perforation and a cut with one or more connection regions. As used herein, the phrase "corner incomplete cut" refers to an incomplete cut that delineates a corner piece, that is, one of the at least two sections of the object delineated by the "corner incomplete cut" is a corner piece. For example, some embodiments of corner incomplete cuts are depicted as lines 6*a*, 8*a*, 10*a*, 12*a* in FIG. 8*b*. In embodiments in which the wound pad is substantially planar, a corner incomplete cut would extend from one edge to an adjacent edge. In various embodiments, wound pads have no, one, or more than one corner incomplete cut(s). As used herein, the phrase "main incomplete cut" refers to an incomplete cut that delineates at least two sections, none of which is a corner piece. For example, some embodiments of main incomplete cuts are depicted as line 14 in FIGS. 3*b*, 4*b*, 6*b*, 7*b*, line 2 in FIG. 4*a*, lines 112 and 113 in FIG. 12, line 40 in FIGS. 2*a*, 4*a*, 4*b*, 5*b*, 6*b*, 7*b*, 8*b*, 9, line 42 in FIG. 8*b*, line 44 in FIG. 5*b*, line 46 in FIG. 6*b*, line 48 in FIG. 7*b*. In various embodiments, wound pads have no, one, or more than one main incomplete cut(s).

A three dimensional object extends in several directions. In particular, it is common to describe an object by referring to its extensions in a length direction, a width direction and a thickness direction. As used herein, the expression "main extension parallel to an X-Y plane" refers to the length and width (of the wound pad) extending parallel to said X-Y plane. This is in contrast to the thickness of the wound pad, which extends perpendicularly to said X-Y plane, i.e. the Z direction. For some substantially symmetrical shapes, such as a substantially square shape or hexagon, the length and width may be considered to be substantially equal.

As used herein, the term "manually separable" refers to the quality of being able to be separated by a typical human adult with his or her bare hands, that is, without the use of utensils, and without extraneous effort. For example, a material that can be easily ripped apart by the majority of adult human users without using utensils is considered "manually separable". A material that cannot be ripped apart, except with the use of utensils and/or except with the use of excessive force is not considered "manually separable".

As used herein, the terms "negative pressure," "vacuum," "suction," "reduced pressure," and "subatmospheric" are used interchangeably and all refer to pressure below normal atmospheric pressure.

As used herein, the term "one-piece" refers to a characteristic of an object in that the object is made entirely of the same material. In some embodiments, a "one-piece" object is also constructed from a single piece of that material. As a non-limiting example, a wound pad that is shaped and cut from a single block of foam material would be considered a "one-piece" wound pad.

As used herein, the term "planar" refers to the shape of an object that is flat and two-dimensional. The term "substantially planar" refers to the shape of an object that is flat and nearly two-dimensional, that is, it may have a non-zero thickness that is significantly smaller than either of the two other dimensions.

As used herein, the term "significantly" refers to its ordinary meaning in the art. For example, when referring to a difference in length or curvature, the term "significantly" as used herein is used to indicate that the difference is meaningful. In some embodiments, when used in the context of a quantifiable feature, the term "significantly different" generally refers to a difference of at least 20%. For example, when referring to differences in radii of curvature, radii of five and six units (e.g., 5 cm and 6 cm) would be considered to be significantly different; larger differences would also be considered significantly different. In some embodiments, a significant difference in a feature that is quantifiable represents a difference of at least 25%, at least 30%, at least 40%, or at least 50%. In some embodiments, a significant difference in a feature that is quantifiable represents a different of at least 50%.

As used herein, the term "sterilized" refers to the state of being substantially free of living microorganisms, or to refer to being subject to a process in order to be substantially free of living microorganisms.

As used herein, the term "substantially" refers to a complete or nearly complete extent or degree of an action, characteristic, property, state, structure, item, or result. For example, an object that is "substantially" rectangular solid in shape is either completely rectangular solid or nearly completely rectangular solid in shape. For example, an object that is shaped such that every cross section along a certain direction has the same shape, and in which that same shape is a rectangle, but with rounded corners, is consider to be substantially rectangular solid. The exact allowable degree of deviation from absolute completeness may in some cases depend on the specific context.

As used herein, the term "structurally intact" refers to the characteristic of an object that can be handled as a one-piece object, and does not fall apart or into pieces when lifted at any part of the object. For example, certain wound pads of the invention may have two or more sections defined by incomplete cuts, but may nevertheless be "structurally intact" because the two or more sections are still connected to one another, e.g., by connection portions.

As used herein, the term "rectangular solid" refers to a three-dimensional object having six faces that are rectangles. Any combination of dimensions in a rectangular solid is possible. For example, the three dimensions of a rectangular solid-shaped object can all differ from each other. Alternatively, two of the dimensions of such an object may be the same, but differ from the third dimension. Alternatively, all three dimensions may be the same. Accordingly, the term "rectangular solid" encompasses "cubic."

As used herein, the term "wound", in addition to having its ordinary meaning in the medical arts, can refer to any body part of a patient (such as a human or animal) that one may desire to subject to a course of treatment.

DETAILED DESCRIPTION OF CERTAIN EMBODIMENTS

The present invention is directed, among other things, to wound pads with features that facilitate shaping and sizing the wound pad into, for example, cavernous wounds of various shapes and sizes. Also provided are systems comprising such wound pads (for example, negative pressure wound treatment systems), kits comprising such wound pads, and methods of using inventive wound pads.

I. Wound Pads

A. Shapes and Dimensions

Wound pads of the invention generally have a shape with corners. As non-limiting examples, wound pads can have any of a number of substantially polygon shapes, such as triangle, trapezoid, rectangular, pentagon, hexagons. Both substantially solid shaped and substantially planar wound pads are contemplated.

In some embodiments, at least one of the corners of the wound pad is rounded. Alternatively or additionally, the wound pad is provided with corner incomplete cuts (as described hereinbelow) at one or more corners, such corner incomplete cuts allowing a user to easily manually separate (e.g., without using utensils) one or more corner pieces of the wound pad, so as to leave at least one rounded corner on the remainder of the wound pad. In some such embodiments, at least a fourth, at least a third, at least a half, at least two-thirds, or at least three-fourths of the corners of the wound pad are rounded. In some embodiments, all corners of the wound pad are rounded.

In some embodiments, the thickness of the wound pad is smaller than the width and smaller than the length.

In some embodiments of the invention, the thickness of the wound pad is significantly smaller than the width and the length, e.g., at most 50%, at most 40%, at most 30%, at most 25%, at most 20%, at most 15%, at least 10%, at most 9%, at most 8%, at most 7%, at most 6%, at most 5%, at most 4%, or at most 3% of the shorter of the width or length dimensions. In some embodiments, the thickness of the wound pad is at most 6% of the shorter of the width or length dimensions. In some embodiments, the thickness of the wound pad is at most 5% of the shorter of the width or length dimensions.

Figure 8A:
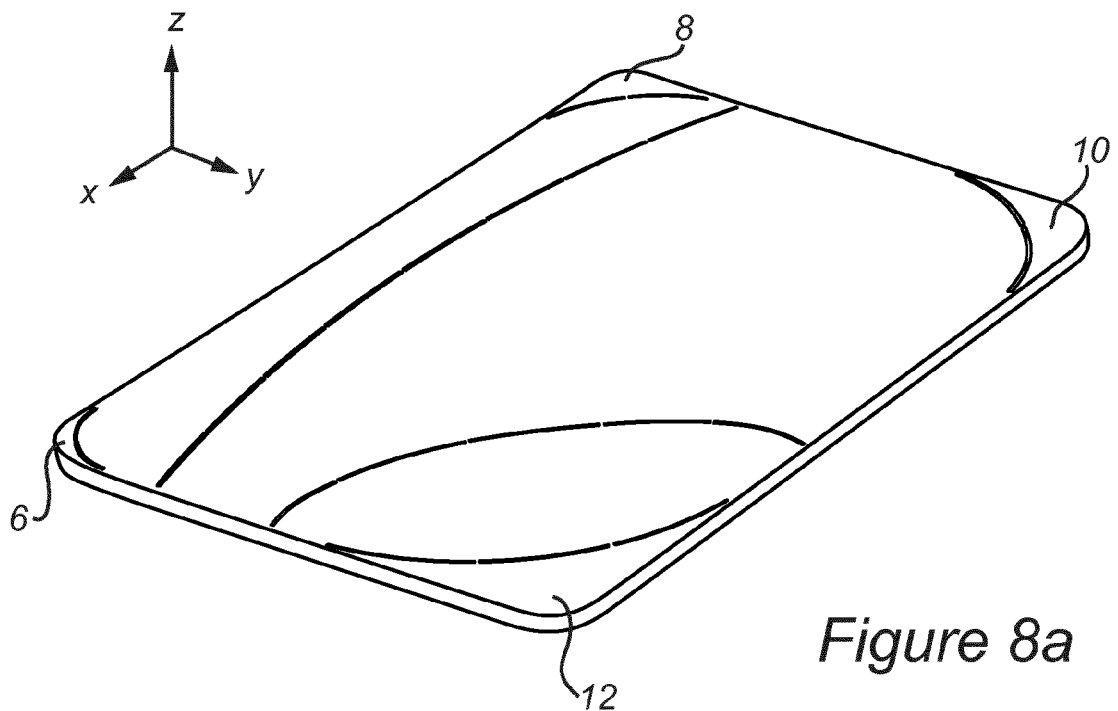
Figure 8B:
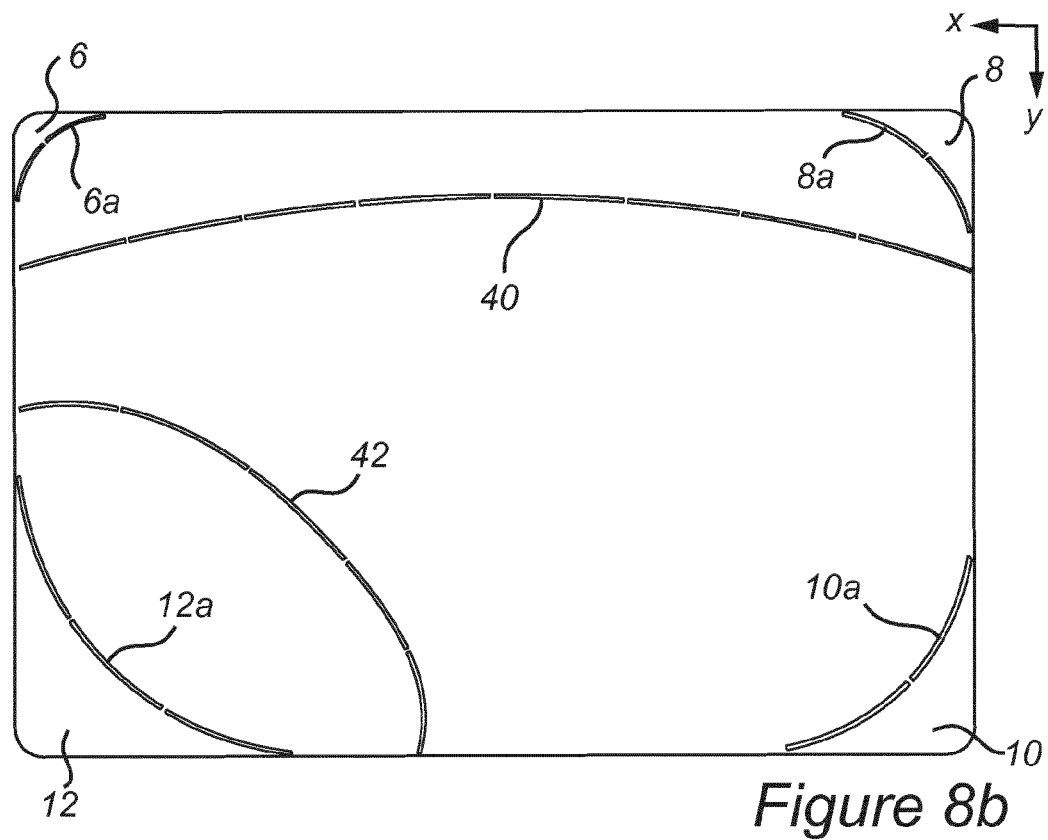
Figure 9:
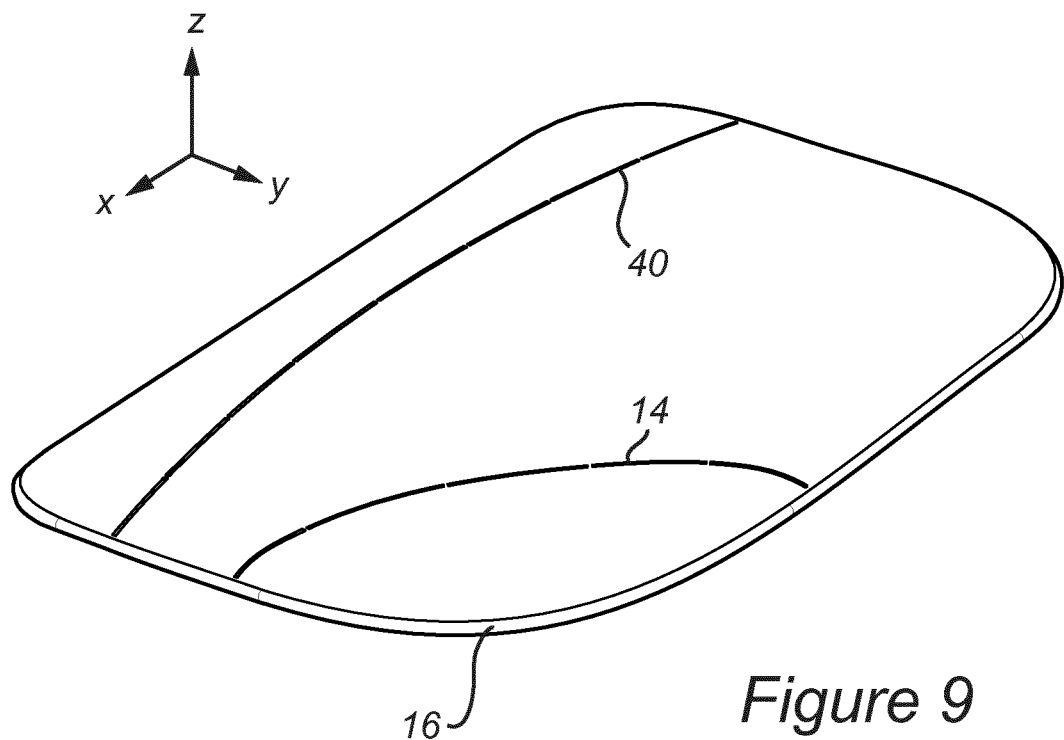
FIG. 9 shows a perspective view of an exemplary wound pad of the invention, similar to the one shown in FIG. 4a, the difference being that the peripheral edge of the wound pad in FIG. 9 does not only have roundness in the circumferential direction of the pad but is also rounded in the direction perpendicular to the circumferential direction, thus presenting a pad without any sharp edges.

In certain embodiments, inventive wound pads are substantially planar and rectangular in shape and can be considered to have four corners, the corners of the rectangle that is formed by the wide and long edges of the wound pad. In some embodiments, at least one of these four corners is provided as a rounded corner with a curvature; removable, by manually separating a corner piece delineated by a corner incomplete cut, so as to leave a rounded corner with a curvature; or both. In some embodiments, all four corners are provided as a rounded corner with a curvature; removable (as described herein) so as to leave a rounded corner with a curvature; or both. FIGS. 1a-7b show examples of embodiments in which all four corners are provided as rounded corners with curvatures, whereas FIGS. 8a and 8b show examples of embodiments in which all four corners are provided with corner incomplete cuts 6a, 8a, 10a, 12a that allow manual separation of corner pieces 6, 8, 10, 12, respectively, so as to leave rounded corners with curvatures. Embodiments of the invention also include wound pads in which some corners are provided rounded, and some corners are shapable into rounded corners as described herein.

Figure 2A:
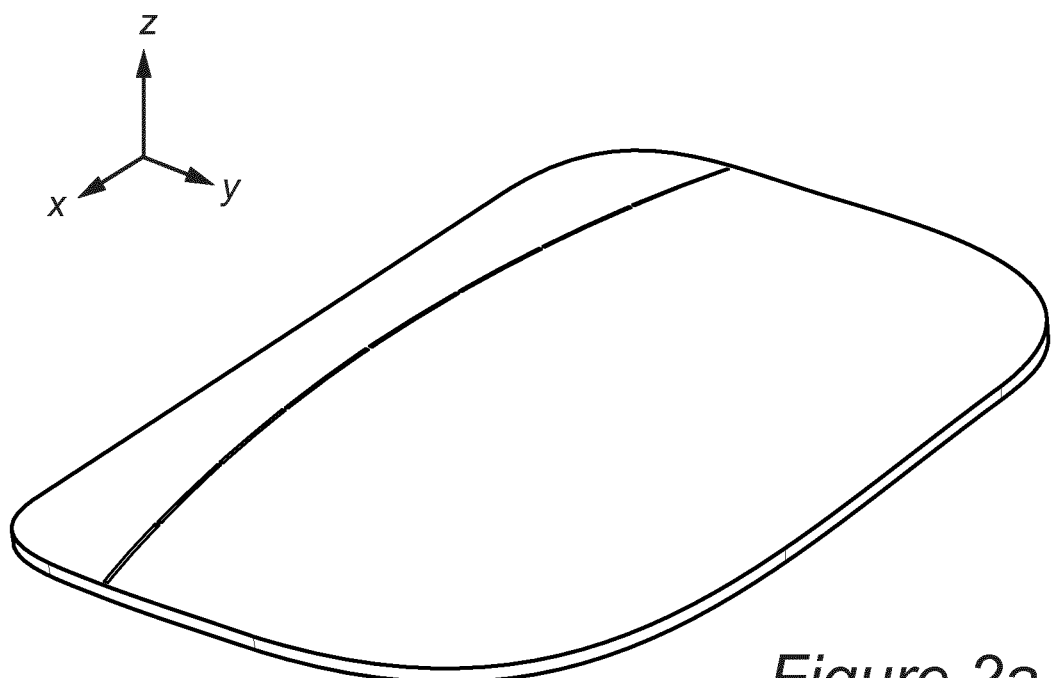
Figure 2B:
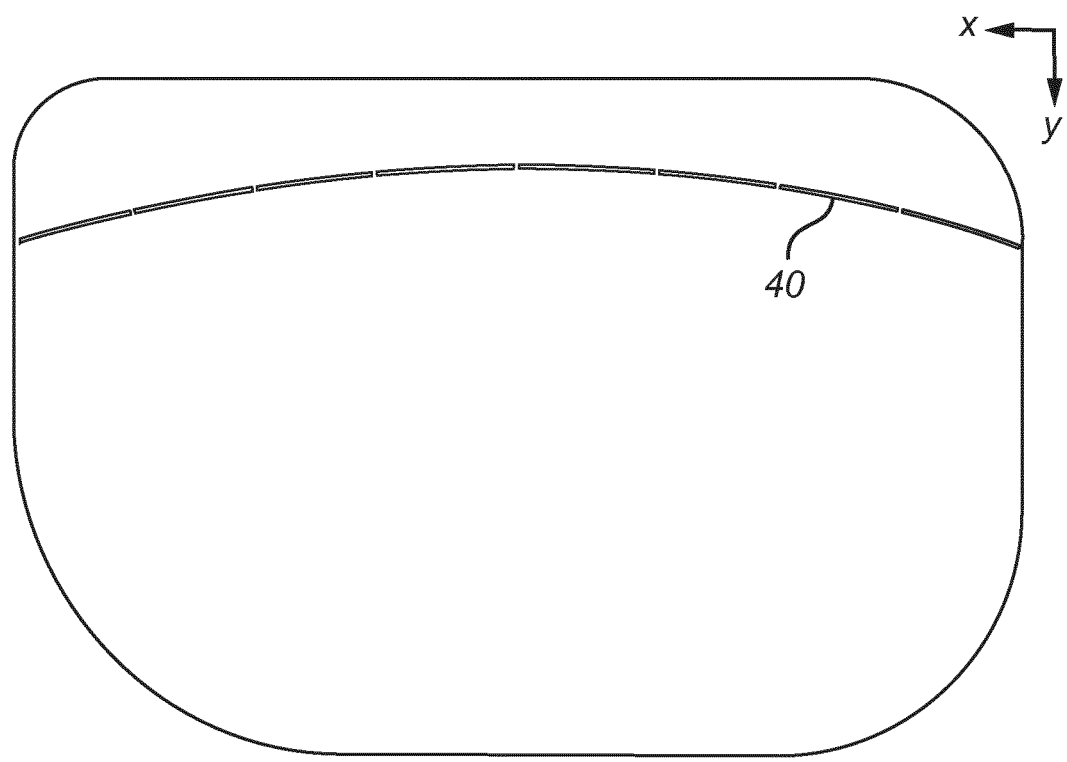
Figure 3A:
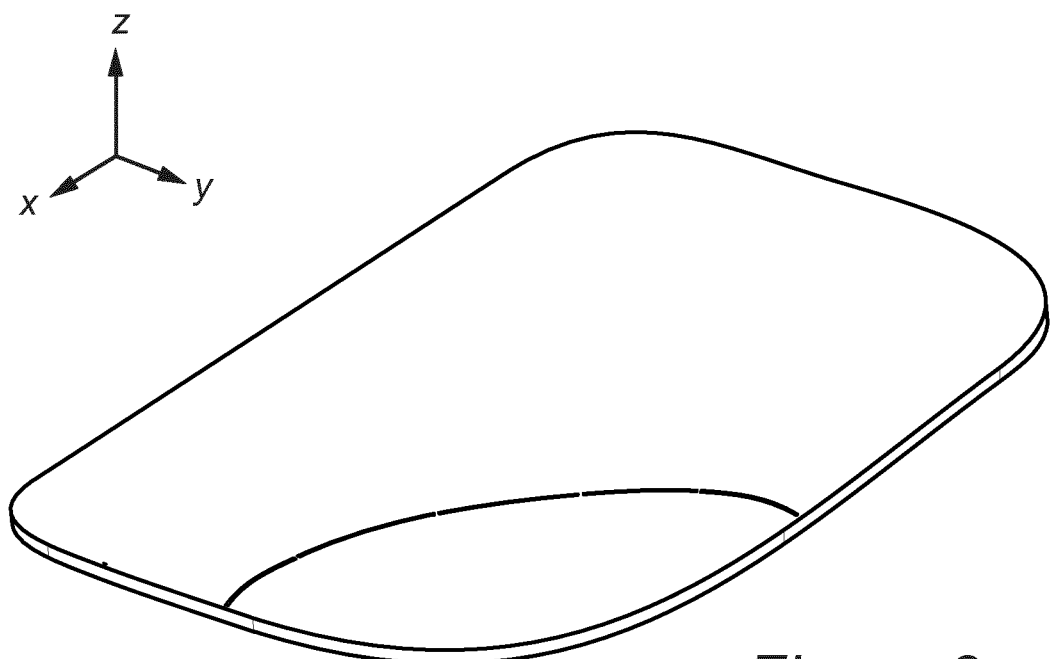
Figure 3B:
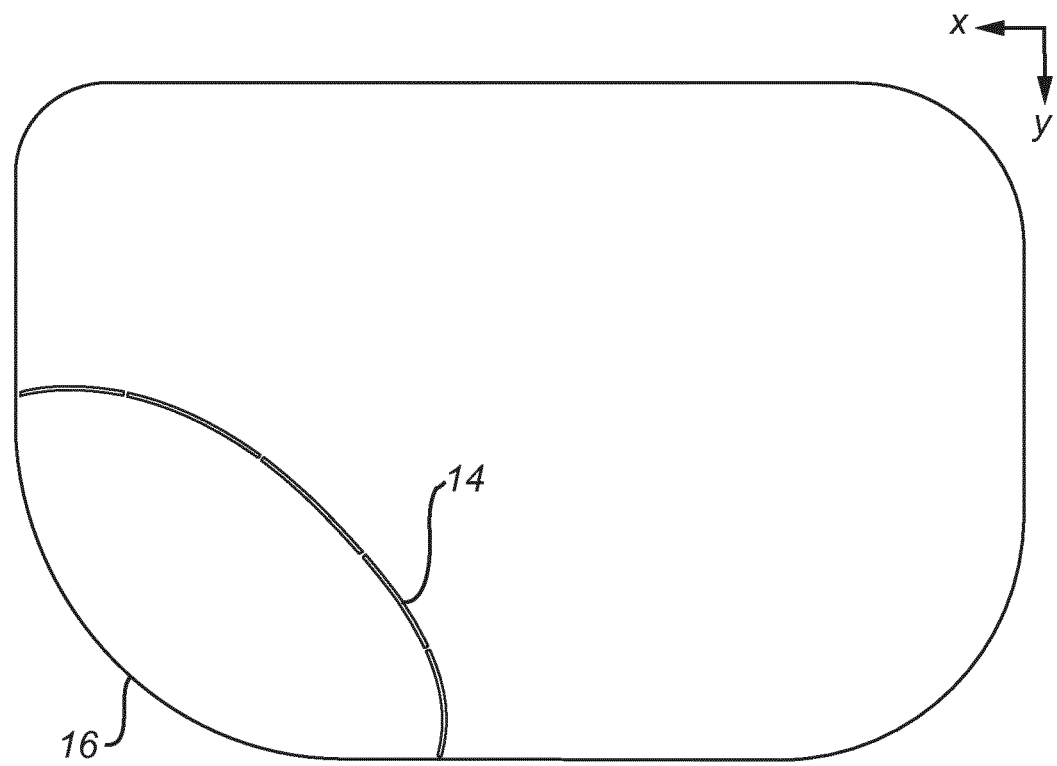
Figure 10:
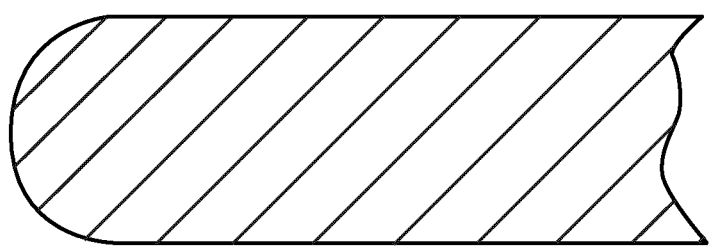
FIG. 10 shows a detailed cross-sectional view of the periphery of the wound pad in FIG. 9.

The roundness of the corner(s) may be limited to the plane of the rectangle defined by the wide and long edges, as shown, for example in FIGS. 1a, 2a, 3a . . . , 8a, where the edge between one surface and other surfaces is sharp. Alternatively or additionally, as exemplified in FIGS. 9 and 10, the corner(s) may be round in all dimensions, so that at the corners, there are no sharp edges encountered when moving from any surface of the wound pad to another plane. It should be noted that other embodiments, such as any one of the wound pads illustrated in FIGS. 1a-8b could be modified to corners being round in all dimensions.

B. Curvatures of Corners

In wound pads of the invention, at least one rounded corner (whether a corner that is already provided rounded, or a rounded corner that is left after manually separating a corner piece at a corner incomplete cut) of the wound pad has a curvature that differs from the curvatures of any of the other rounded corners. In some embodiments, the curvature of the at least one rounded corner differs significantly from the curvature of any of the other rounded corners.

The number of different curvatures provided in a single wound pad varies depending on the embodiment. Generally, the non-uniformity of the curvatures of the wound pad allows increased flexibility for a user (e.g., a clinician and/or patient) in being able to shape and size the wound pad appropriately. As further described herein, a user can, for example, choose a rounded corner with the most appropriate size and shape for fitting into one part of the wound, and shape the rest of the wound pad into the rest of the wound as necessary. Wound pads of the invention thus offer the potential to reduce the amount of cutting with utensils needed to fit them into a wound cavity.

Table 1 shows non-limiting examples of possible schemes for some embodiments in which the wound pad is substantially planar and each of the four corners are provided rounded; provided with corner incomplete cuts so as to allow easy removal of a corner piece, leaving a rounded corner; or both. In Table 1, the designation of a corner as the "first corner" is arbitrary. The second, third, and fourth corners are corners defined relative to "the first corner" in a clockwise direction. Corners having the same curvature are designated by the same letter, while different letters are used to designate that the corners have different curvatures.

As shown in schemes 1-4 of Table 1, in some embodiments, one of the four rounded corners has a curvature differing from that of the other three, while the other three have substantially similar curvatures with each other. In some embodiments, at least two of the rounded corners have curvatures that differ from the other rounded corners (for example, see schemes 5-12 in Table 1). In some such embodiments, the curvatures of the at least two rounded corners differ from each other. (For example, see schemes 8-12 in Table 1), while in other such embodiments, the curvatures of the at least two rounded corners are substantially similar. (For example, see schemes 5-7 in Table 1). In some embodiments, the rounded corners collectively have at least three different curvatures. (For example, see schemes 8-12 in Table 1). In some embodiments, a total of four different curvatures is used, such that each rounded corner is distinct from one another in curvature. (For example, see scheme 12 in Table 1.)

TABLE 1

Non-limiting examples of rounded corner schemes in substantially planar wound pads of the invention

| Scheme | First corner | Second corner | Third corner | Fourth corner |
|---|---|---|---|---|
| 1 | A | A | A | B |
| 2 | A | A | B | A |
| 3 | A | B | A | A |
| 4 | A | B | B | B |
| 5 | A | A | B | B |
| 6 | A | B | B | A |
| 7 | A | B | A | B |
| 8 | A | B | C | A |
| 9 | A | B | A | C |
| 10 | A | A | B | C |
| 11 | A | B | B | C |
| 12 | A | B | C | D |

As a non-limiting example, a rounded corner can have a curvature that is an arc of a circle or an ellipse, and the radius of the circle or the radii of the ellipse can be a feature of the curvature. Such a feature may vary between one rounded corner and another rounded corner. Thus, one of the non-limiting ways in which curvatures can differ is by having different radii of curvature.

For example, in some embodiments in which the wound pad is substantially planar and rectangular, the four rounded corners (whether provided as a rounded corner having a curvature, removable by manually separating a corner piece at a provided corner incomplete cut so as to leave a rounded corner having a curvature, or both) each have curvatures that may vary in their radii of curvature, so long as at least one rounded corner has a different radius of curvature than the radii of curvature of any of the other rounded corners. In some embodiments, the difference in the radii is significant. In some embodiments, at least one radius of curvature differs from any of the other rounded corners by at least 20%, at least 25%, at least 30%, at least 40%, or at least 50%.

In some such embodiments, all four rounded corners have different radii of curvature, and these different radii of curvature are chosen so that they collectively span a large range, thereby increasing the chance that at least one of the rounded corners can fit substantially well into the wound cavity. For example, in some embodiments, the radii of curvature of the rounded corners, in order from the smallest to largest radii of curvature, substantially have a ratio of 1:2:3:4. Examples of some such embodiments are depicted in FIGS. 1a-9.

In some embodiments in which the wound pad is substantially planar and rectangular, each of the four corners is provided as a rounded corner and is also removable, by manually separating a corner piece at a provided corner incomplete cut, so as to leave a rounded corner having a different curvature than that of the provided rounded corner. Thus, not only is each corner already rounded with a particular curvature, there is also a possibility to obtain a rounded corner of a different curvature by using a provided corner incomplete cut at the corner. Thus, there is the potential to increase the number of different curvatures of rounded corners available (as either already provided or shapable without utensils as described herein) to eight.

It should be understood that although embodiments of substantially planar and substantially rectangular wound pads are discussed herein for illustrative purposes, the invention encompasses wound pads of different shapes including non-rectangular and/or non-planar shapes.

C. Incomplete Cuts

In some embodiments, inventive wound pads are provided with one or more main incomplete cuts, each incomplete cut delineating a section of the wound pad that can be manually separated from the rest of the wound pad. By "incomplete" it is meant that the structural integrity of the wound pad is maintained. Thus, the wound pad can be handled as a one-piece wound pad despite the provision of one or more main incomplete cuts.

Accordingly, different sizes and shapes of wound pads can be created by pulling the wound pad apart at the one or more provided main incomplete cuts, without using utensils. Also as mentioned herein, in some embodiments, wound pads comprise one or more corners that are removed, by manually separating a corner piece delineated by a corner incomplete cut, so as to leave a rounded corner with a curvature.

Both main incomplete cuts and corner incomplete cuts can be formed on wound pads of the invention using any suitable mechanism, including, but not limited to, blade cutting, die cutting, and hot wire cutting. Alternatively or additionally, incomplete cuts can be created by placing together separate sections of wound pads that fit together, like pieces of a puzzle, and then joining the sections at particular connection regions. Joining of the sections may be accomplished by any of a variety of known methods of the art, including, but not limited to, using adhesives and/or welding (e.g. ultrasonic welding and/or dot welding).

Incomplete cuts can be, for example, provided as multiple small perforations. Alternatively or additionally, incomplete cuts can be provided as mostly continuous cuts, interrupted by one or more regions that remain uncut (herein "connection region"). Referring to both the perspective and the enlarged detailed views in FIG. 4a, a wound pad is provided with main incomplete cuts 2 and 40 (cut 2 shown in detail) that comprise connection regions 4. Connection regions may or may not be evenly spaced across the main incomplete cut. Similarly, a wound pad may be provided with corner incomplete cuts, as e.g. shown in FIGS. 8a-8b, which may likewise comprise connections regions. Connection regions may or may not be evenly spaced across the corner incomplete cut.

In some embodiments wherein the wound pad is substantially planar, at least one of the incomplete cuts (corner and/or main incomplete cuts) extends through at least a portion of the thickness of the wound pad. In some such embodiments, incomplete cuts extend entirely through the thickness of the wound pad, except at the one or more connection regions. At each of the one or more connection regions, there may be no cut at all or there may be one or more cuts that each extend only through a portion of the thickness of the wound pad, such that at least some part along the thickness of the wound pad remains intact.

In some embodiments, at least one main incomplete cut extends from one edge of the wound pad to another edge of the wound pad. In some embodiments, at least one main incomplete cut extends from one edge to an opposite edge.

In some embodiments, at least one main incomplete cut extends from one edge to an adjacent edge.

In some embodiments wherein the wound pad is substantially planar and substantially rectangular, one dimension of the rectangle is significantly shorter than the other dimension of the rectangle. Therefore two of the edges of the rectangle can be considered the short edges (corresponding to the shorter dimension) and the other two edges of the rectangle can be considered the long edges. In some embodiments, at least one incomplete cut (main or corner) extends from a short edge to a long edge. In some embodiments, at least one main incomplete cut extends from a short edge to another short edge. In some embodiments, at least one main incomplete cut extends from a long edge to another long edge.

In some embodiments, no incomplete cut extends through (e.g., crosses) another incomplete cut.

In some embodiments, at least one main incomplete cut extends through (e.g., crosses) another main incomplete cut.

Main incomplete cuts can be in any of, a variety of, and/or a combination of shapes, for example, substantially linear, substantially arcuate (including one or more arcs from circles and/or ellipses), substantially zigzag, etc. In some embodiments, main incomplete cuts are substantially arcuate in shape. Some such arcuate shapes may be one or more arcs from a circle or ellipse, and are therefore characterized by one or more curvatures. Combinations of shapes can also be used, for example, partly linear and partly zigzag, partly arcuate and partly linear, entirely arcuate but comprised of at least two different arcs, etc.

The number of main incomplete cuts provided in a wound pad may vary depending on the particular embodiments. Some inventive wound pads are not provided with any main incomplete cuts at all (See, e.g. FIGS. 1a and 1b), whereas some are provided with at least one main incomplete cut, some are provided with at least two main incomplete cuts, some are provided with at least three main incomplete cuts, etc.

The number of corner incomplete cuts provided in a wound pad may vary depending on the particular embodiments. Some inventive wound pads are not provided with any corner incomplete cuts, whereas others are provided with the maximum number of corner incomplete cuts (i.e., the maximum number of corners pieces in the wound pad), whereas other inventive wound pads are provided with some, but less than the maximum number of corner incomplete cuts. For example, for wound pads that are both substantially planar and substantially rectangular, the wound pad may be provided with no, one, two, three, or four corner incomplete cut(s).

For example, FIGS. 2a-8b show examples of embodiments of substantially planar wound pads that comprise one or more main incomplete cuts 2, 14, 40, 42, 44, 46, 48 whose shapes are each substantially arcuate. Embodiments shown in FIGS. 8a and 8b comprise corner incomplete cuts 6a, 8a, 10a, 12a that allow the corners to be removed by manually separating one or more corner pieces 6, 8, 10, 12, so as to leave rounded corners having curvatures. In some embodiments, wound pads are provided with at least one arcuate main incomplete cut that extends from one edge to an adjacent edge, the two edges being joined by a rounded corner having a curvature. In some such embodiments, the curvature of the arcuate main incomplete cut is substantially the same as the curvature of the rounded corner that joins the two edges. Thus, the arcuate main incomplete cut and the rounded corner form a symmetric shape comprised of two substantially equal arcs. Examples of such embodiments are shown in FIGS. 3b, 4b, 6b, 7b and 9, in which the arcuate main incomplete cut 14 and rounded corner 16 form a symmetric shape comprised of two substantially equal arcs.

D. Material Composition

Any of a number of suitable materials can be used in the practice of the invention.

Features of the invention are particularly suitable for wound pads made of less conformable (e.g., at least semi-rigid) materials that are difficult to fit into a wound without modifying the size and/or shape of the wound pad.

For example, some inventive wound pads may comprise a foam, for example, a semi-rigid foam.

In some embodiments, inventive wound pads comprise a porous foam. The porous foam may be, for example, an open-cell foam. Alternatively or additionally, inventive wound pads may comprise a closed-cell foam that comprises through-holes. The through holes may extend through the entirety of one dimension (e.g., the thickness) of the wound pad. Such embodiments may allow fluid to flow through the wound pad, and may be particularly suited for use in negative pressure wound treatment systems as described hereinbelow. Porous foams may be made of any suitable material, including, but not limited to, polymer foams as described herein.

In some embodiments, inventive wound pads comprise a polymer foam, which may or may not be porous. Non-limiting examples of suitable polymer foams include polyurethane foams, polyester foams, polyether foams, polyvinyl alcohol foams, silicone foams, and combinations thereof. In some embodiments, the polymer foam comprises a polyurethane foam.

In some embodiments, inventive wound pads are hydrophobic. As a non-limiting example, AVANCE™ Foam sold by Mölnlycke Health Care is made of a hydrophobic reticulated polyurethane foam with a large open cell structure. Such a material is also suitable for making wound pads of the present invention.

In some embodiments, inventive wound pads are hydrophilic or treated with an agent that makes the foam hydrophilic.

In some embodiments, inventive wound pads, including their corners pieces, are suitable for use as a wound filler. Thus, an entire wound pad may be made of a material or materials suitable for application inside an open wound. Such a wound pad, including its corner pieces, may suitably comprise a foam of the types mentioned in the above disclosed embodiments (for instance, a porous foam, such as an open-cell foam, e.g. a polymer foam).

E. Dimensions

Wound pads of the invention may be made in any suitable size. Contemplated embodiments include, but are not limited to, large wound pads, and in particular, large wound pads that are substantially planar and rectangular in shape. For example, some inventive wound pads have a length and a width each of at least about 25 cm and a thickness of between about 0.75 cm and about 3 cm (such as, for example, about 0.75 cm, about 1 cm, about 1.5 cm, about 2 cm, about 2.5 cm, or 3 cm). In some embodiments, the thickness of wound pad is about 1 cm or about 1.5 cm. As a non-limiting example, some inventive wound pads are approximately 45 cm length by 30 cm width by 1.5 cm thickness.

F. Sterilization

In certain embodiments of the invention, provided wound pads and kit components are sterilized so that they are medically acceptable, e.g., appropriate for use in wound care. Sterilization can be achieved by any one or a combination of known protocols in the art, some of which are standardized and approved by regulatory bodies. Non-limiting examples of sterilization methods for wound care products include autoclaving, exposure to dry heat, exposure to ultraviolet radiation, ethylene oxide treatment, gamma irradiation, immersion in aqueous alcohol solutions (e.g., 70% or greater concentrations of ethanol), gas plasma technology, steam sterilization, and electron beam irradiation. The choice of sterilization method can be influenced by a factor such as the type of material, which may have varying abilities to withstand and/or retain desirable characteristics under different sterilization protocols. For example, some ethylene oxide treatment protocols are well suited for sterilization of polymer foam materials.

II. Negative Pressure Wound Treatment Systems and Kits

A. Systems

I In one aspect of the invention, provided are systems for negative pressure wound treatment that comprise a negative pressure source for providing negative pressure to a wound, a wound pad of the invention as described herein, a wound cover disposed over the wound with the wound pad in it, and a conduit configured to transmit negative pressure from the negative pressure source to the wound. The conduit is fluidly coupled at one end (hereinafter the "proximal end") to the wound and at one end (hereinafter the "distal end") to the negative pressure source. In some embodiments, the proximal end of the conduit is placed into the wound underneath the wound cover. In some embodiments, the proximal end of the conduit is placed above the wound cover and fluidly connected to the wound cavity via a hole or port in the wound cover. The wound cover can be supplied with a hole or port, and/or a hole or port can be created for such a purpose.

In some embodiments, systems further comprise any or a combination of: one or more wound contact layers disposed inside the wound beneath the wound pad, a wound interface device between the conduit and the wound cover, and/or a storage canister in fluid communication with the conduit for collecting fluid such as wound exudate. In embodiments comprising a storage container, a filter may be included to prevent fluids, aerosols, and/or other contaminants from leaving the container.

Figure 11:
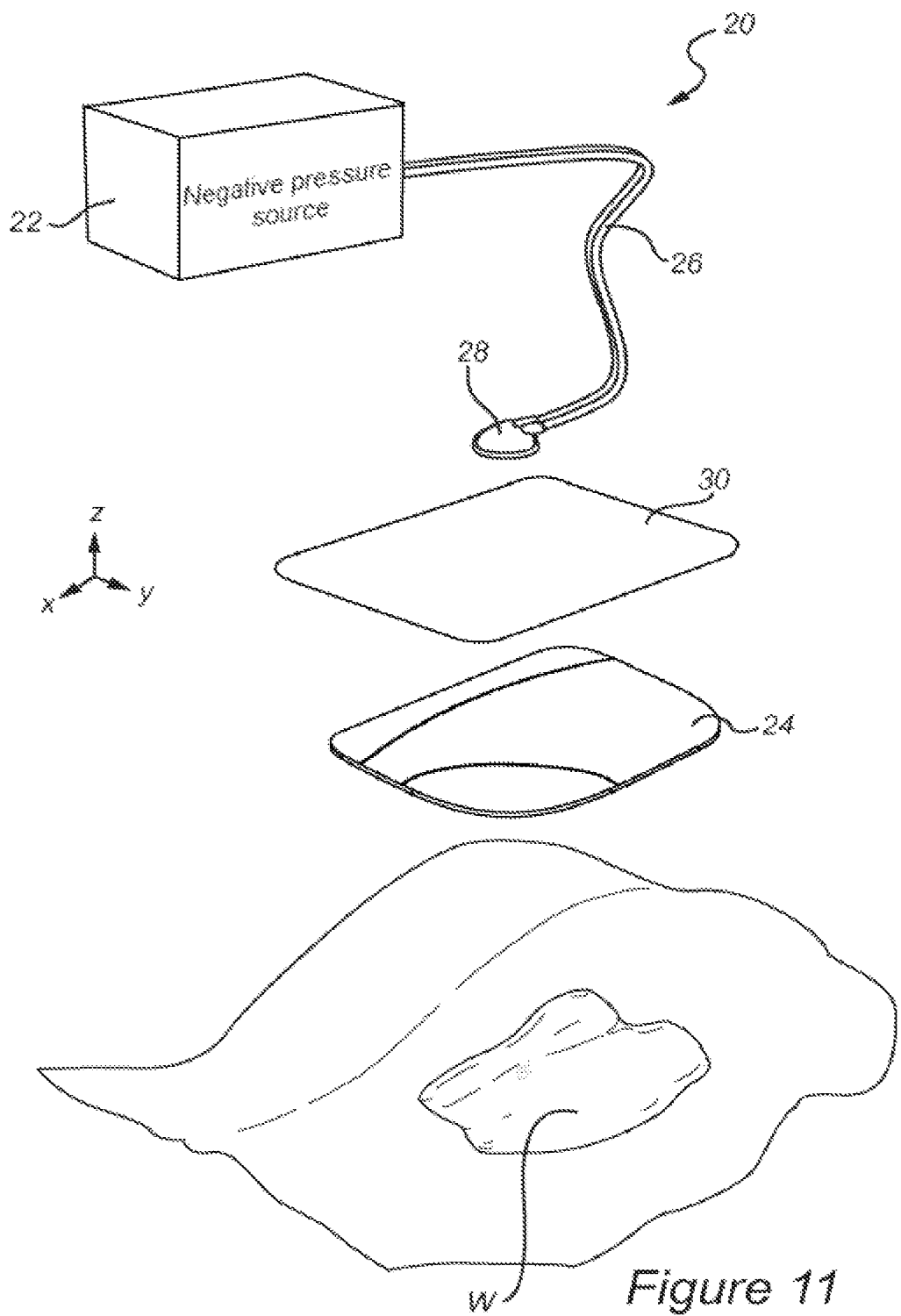
FIG. 11 shows a system according to at least one aspect of the invention, which system comprise a wound pad and a negative pressure source for providing negative pressure to a wound.

An exemplary embodiment of a system for negative pressure wound treatment is illustrated in FIG. 11. The system comprises a negative pressure source 22 for providing negative pressure to a wound W, a wound pad 24 of the invention as described herein to be placed into the wound, and a wound cover 30. A conduit 26 is configured to transmit negative pressure from the negative pressure source 22 to the wound W. In FIG. 11, the shown conduit is a multi-lumen conduit with a parallel lumen configuration; however, as explained below, a single lumen and/or other multi-lumen configurations may be used. An optional interface device 28 is also shown, although contemplated embodiments include those without interface devices.

Negative Pressure Sources

The negative pressure source may comprise a pump, non-limiting examples of which include vacuum pumps (e.g., electrically-driven vacuum pumps, manually actuated pumps, piezoelectric-actuated pumps, etc.), circulation pumps, dual action vacuum/pressure pumps (e.g. for drainage and irrigation), peristaltic pumps, syringe pumps, bellows pumps, diaphragm pumps, and combinations thereof. Pumps in systems of the invention are generally adapted to provide a negative pressure value that is suitable for treatment protocols standard in the art. In some embodiments, the negative pressure source includes one or more pressure sensors for detecting a pressure within the system.

Depending on the embodiments, the negative pressure source may be adapted to provide negative pressure at a fixed negative pressure value or may be adapted to provide negative pressure at one of multiple values which may be selected, for example, by the user and/or depending on the therapy mode. In some such embodiments, the negative pressure source is adapted to provide negative pressure at various values within a range. In some such embodiments, the negative pressure source is adapted to provide negative pressure at any value in certain increments from a lower limit (absolute value) to an upper limit (absolute value).

The negative pressure source may be adapted to provide negative pressure continuously during treatment. Alternative or additionally, the negative pressure source is adapted to provide negative pressure intermittently during treatment.

Generally, the negative pressure source is adapted to provide negative pressure at one or more values that fall within the range between about 20 mmHg and about 400 mHg (inclusive of endpoints).

For example, typical threshold values used during negative pressure wound therapy include any value in the range between about 20 mmHg and about 400 mmHg (inclusive of both endpoints), for example, about 20 mmHg, about 25 mmHg, about 50 mmHg, about 60 mmHg, about 80 mmHg, about 120 mmHg, about 200 mmHg, or about 300 mmHg. For example, in some embodiments, a negative pressure of about 80 mmHg is used. In some embodiments, a negative pressure of about 120 mmHg is used.

The selection of the appropriate values may be made, for example, by a clinician or patient. The choice of appropriate negative pressure value(s) may be influenced by any or a combination of factors such as location of wound, type of wound, wound healing status, type and/or material of wound pad, type of dressing, patient, etc. In some embodiments where the wound pad is comprised of a polymer foam, a negative pressure of about 120 mmHg is used.

In some embodiments, the negative pressure source may be adapted to provide a negative pressure, the absolute value of which is greater than or equal to about 120 mmHg or about 180 mmHg.

Wound Covers

Any of a variety of wound covers compatible with negative pressure wound treatment systems can be used. Generally, the wound cover is adapted to be attached to the skin surrounding the wound, and, either alone or in combination with one or more other components of the negative pressure system, forms an airtight seal over the wound. Non-limiting examples of suitable wound covers include plastic films, e.g. polyurethane films.

The wound cover can be attached to the skin surrounding the wound, for example, by means of an adhesive. Wound covers may comprise an adhesive, and/or by used with an adhesive that is applied just before use. Examples of adhesives that may be used include, but are not limited to, acrylic adhesives and/or silicone gel adhesives. In some embodiments, the adhesive or adhesives is/are already incorporated as part of the wound cover. In some embodiments, the adhesive or adhesives is/are applied to the wound cover member during use.

For example, a suitable wound cover is AVANCE™ Transparent Film sold by Mölnlycke Health Care AB, which is a polyurethane film with an acrylic adhesive. Also suitable for use in embodiments of the invention is AVANCE™ Film with SAFETAC™ technology (also sold by Mölnlycke Health Care AB), which comprises a layer of perforated polyurethane coated on one side with silicone gel. As a non-limiting example, the adhesive sold under the trademark MEPISEAL™ by Mölnlycke Healthcare AB may be used for attaching the wound cover member to the skin surrounding the wound.

Conduits

In some embodiments, the conduit is provided via a single lumen tube.

In some embodiments, the conduit is provided as part or all of a multi-lumen tube, for example, wherein one lumen is used to provide negative pressure to the wound, and one or more additional lumens may be used for another purpose, e.g., circulation, measurement (e.g. of pressure), irrigation, etc. In embodiments with multiple lumens, any of a variety of possible arrangements of the lumens is possible, e.g., parallel lumen arrangements, central and peripheral lumen arrangements, etc.

In some embodiments, fluid is transported via the conduit. For example, wound exudates may be transported away from the wound via the conduit. In embodiments with a canister, wound exudates may be transported into the canister.

Wound Contact Layers

In some embodiments, provided systems also comprise one or more wound contact layers disposed inside the wound beneath the wound pad. Such wound contact layers are generally made of a biocompatible material and, may, for example, help prevent sticking of the wound to the wound pad. For example, one suitable wound contact layer is the MEPITEL™ dressing sold by Mölnlycke Health Care AB, which is a perforated polyamide fiber elastic material coated on both sides with a tacky soft silicone gel. As a further example, the MEPITEL™ One dressing (also sold by Mölnlycke Health Care AB) is a perforated polyurethane sheet coated on one side (which side can be used as the wound-contacting side) with a tacky silicone gel.

Wound Interface Devices

In some embodiments, provided systems comprise a wound interface device (a device that provides an interface between the conduit and the wound cover). Such wound interface devices are adapted to allow sealed passage of fluid (e.g. gas and/or liquid) between the wound and the conduit. In some embodiments, a hole or port through the wound cover is created and/or provided by the interface device to allow flow of fluid out of and/or into the wound to the conduit. Non-limiting examples of wound interface devices suitable for such purposes and known in the art include the AVANCE™ Transfer Pad sold by Mölnlycke Health Care AB as part of a kit for negative pressure wound treatment.

Canisters

In some embodiments, a canister is provided and arranged so as to allow collection of fluid from the wound (e.g., wound exudates) via the conduit. For example, the conduit may be provided in two parts, one connecting the wound to the canister, and the other connecting the canister to the negative pressure source. Thus, while negative pressure is transmitted from the negative pressure source to the wound via the conduit, fluid may also be drawn from the wound and collected into a canister.

B. Kits

In one aspect of the invention, provided are kits for use in negative pressure wound treatment. Such kits generally comprise at least one wound pad of the invention as described herein, along with at least one item selected from the group consisting of: a wound contact layer as described herein, a wound cover as described herein, and a device that provides an interface between a wound and a conduit ("wound interface device", as described herein).

III. Uses

A. Wounds and Medical Contexts

Generally, inventive wound pads may be used with any cavity wound, whether chronic or traumatic, in any medical context where it is desirable to fill the wound, for example, during at least part of a course of treatment. Non-limiting types of cavity wounds include open wounds, pressure ulcers ("pressure sores"), diabetic ulcers, and burns. Open wounds include both surgically created and non-surgically created wounds. For example, open wounds in the abdominal or peritoneal cavity can be filled using wound pads of the invention.

Wound pads, systems, and kits of the invention may be used for wounds in any part of the body.

In some embodiments, inventive wound pads, systems, and/or kits, are used during the course of negative pressure wound treatment, during which negative pressure is applied to a wound to facilitate healing of a wound and/or closure of a wound.

B. Methods of Using

Wound pads of the invention may be placed and fitted into a cavity wound using, for example, any of the inventive methods described below. These methods generally comprise a step of choosing one of the rounded corners based on the suitability of the rounded corner's curvature with the size and shape of at least part of the wound, placing the chosen corner into the wound, and fitting the rest of the wound pad into the wound.

Because the curvature of at least one rounded corner differs significantly from the curvature of the other rounded corners, there are at least two different curvatures from which a user can choose. Typically the rounded corner whose curvature most closely matches the size and shape of a part of the wound is chosen. In some embodiments, the chosen rounded corner does not need to be further shaped or sized, as its curvature matches closely a part of the wound.

In some embodiments, the chosen rounded corner is further shaped and/or sized in order to better fit a part of the wound.

To determine the suitability of the corner's curvature with the size and shape of at least part of the wound, the wound's general dimensions and shape is typically first inspected, e.g., visually. Such an inspection may involve one or more of lifting parts of the patient's skin or flesh, shining light into the wound, feeling inside the wound with a hand or one or more tools, measurement of the wound, or a combination thereof.

In some embodiments, the chosen rounded corner is provided as rounded.

In some embodiments, the chosen rounded corner is obtained by pulling away a corner piece from the rest of the wound pad at a provided corner incomplete cut (i.e., removing the corner piece, thereby leaving a rounded corner. The provided corner incomplete cut facilitates the removal of the corner piece without the use of utensils.

In some embodiments, the curvature of the chosen rounded corner matches the curvature of a part of the wound cavity such that no alterations of the chosen corner are needed. In some embodiments, even if the most suitable rounded corner is chosen, the chosen rounded corner is altered to enhance the fit of the corner into a part of the wound.

In some embodiments, methods comprise additional steps, each of which may be performed before or after any of the aforementioned steps. Alternatively or additionally, an additional step may be performed as part of the step of fitting the rest of the wound pad into the wound.

For example, in embodiments in which the wound pads are provided with main incomplete cuts, it is also possible (though not necessary) to manually separate sections of the wound pad at one or more of the main incomplete cuts in order to obtain a piece of wound pad that is at least more suitable for fitting into a wound than the originally provided wound pad. Although provided main incomplete cuts make it possible to manually separate a section or sections from the rest of the wound pad, a user may choose nonetheless to use utensils such as scissors.

The features of the invention notwithstanding, it is contemplated that in some embodiments of practicing the invention, a user may choose to use utensils to further size and shape the wound pad. Thus, it is anticipated that in some embodiments, features of inventive wound pads reduce, but do not necessarily eliminate, the amount of altering done to the wound pad with utensils. If any alteration to the size and/or shape of the wound pad with a utensil is performed, such a step can be performed one time or more than one time with each use, and at any time relative to the other steps, for example, before or after choosing one of the corners; before or after fitting one of the rounded corners into the wound; before, after, or in between rounds of using one or more of the main incomplete cuts to manually separate one or more sections of the wound pad.

In some embodiments, more than one wound pad is used to fill the cavity of the wound. All wound pads used may be inventive wound pads, or a combination of one or more inventive wound pads and one or more other wound pads may be used.

In negative pressure wound treatment contexts, a wound is first typically cleaned in a medically acceptable manner, e.g., in a sterile manner. Optionally, a wound dressing that serves as a wound contact layer may be place into the wound cavity, so that it covers at least some of the surface of the wound that might come into contact with a wound pad of the invention. A wound pad is then placed into the wound cavity as described herein.

The wound with the wound pad inside it may be covered with a wound cover that seals the wound at least along the edges of the wound cover, and a conduit is added in a configuration to transmit negative pressure from a negative pressure source to the wound. For example, in some embodiments, the conduit is fluidly connected to the wound through a hole or port created and/or supplied in the wound cover. If a hole is created or supplied in the wound cover, an airtight seal is nonetheless formed over the wound with the wound cover and conduit, due to the design of the interface between the conduit and the wound cover, an additional device that provides an airtight interface between the conduit and the wound cover (a "wound interface device"), use of a sealant, or a combination thereof.

In some embodiments, the conduit is placed into the wound before the wound is covered with a wound cover, and an air tight seal is formed with the optional aid of an adhesive and/or adhesive film.

The conduit may be already connected to a negative pressure source, or may be placed in connection to a negative pressure source during use.

EXAMPLES

The following examples describe some of the modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Wound Pad

Wound pads having the general shape and cut lines as shown in FIGS. 1a-9 were made of a hydrophobic reticulated polyurethane foam material, with approximate dimensions of 45 cm length by 29.5 cm width by 1.5 cm thickness. (Length and width measurements were taken at the middle of the width-wise and length-wise respectively). As shown in FIGS. 1a-7 and 9, these wound pads were substantially planar and substantially rectangular in shape, with four rounded corners. The curvatures of each of these four corners differed from one another. Although all corners were curved as circular arcs, they had different radii of curvature. In the present example, the curvature radii of the corners were (moving clockwise from one corner to the next) approximately 3.75 cm, 7.5 cm, 11.25 cm, and 15 cm.

The foam material is biocompatible and has a large open cell structure, about 5-9 cells per centimeter, a density of about 27-33 kg/m$^3$, a dry tensile strength of about 165 kPa, and a wet tensile strength of about 125 kPa.

Wound pads having one or more cut lines were easily manually separated by adult human users by pulling apart one or more sections of the wound pads at one or more of the provided cut lines.

Example 2

Use as a Wound Filler

A large cavity wound is cleaned with 0.9% saline. The healthy skin surrounding the wound is dried and a protective cream or ointment is applied to the healthy skin. The wound is kept moist.

A wound pad of the invention, such as those described in Example 1, is shaped by first finding the most appropriate corner for the size and shape of the wound cavity. The most appropriate corner of the wound pad placed into the wound first. Some trimming of the most appropriate corner, e.g., with scissors, may be used if appropriate. The rest of the wound pad is sized and shaped to fit the wound cavity by removing one or more sections of the wound pad at one or more cut lines, cutting the wound pad with scissors, or both.

The wound with the wound pad inside it is covered with a secondary dressing that is appropriately chosen for the exudate level of the wound.

Example 3

Use as a Wound Filler During Negative Pressure Wound Treatment

A wound pad as described in Example 1 is used to fill a wound cavity as described in Example 2, except that no secondary dressing is used, and the use of a protective cream or ointment is optional. A wound cover is placed over the wound cavity (with the wound pad inside it), extending over the edges of the wound and forming a seal with the skin on the edges of the wound. A hole is then cut in the wound cover, and the conduit with the wound interface device is arranged with the hole aligned so that negative pressure can be transmitted from the negative pressure source to the wound. The conduit is connected to a negative pressure source, which is then switched on.

Example 4

Wound Pad

Figure 12:
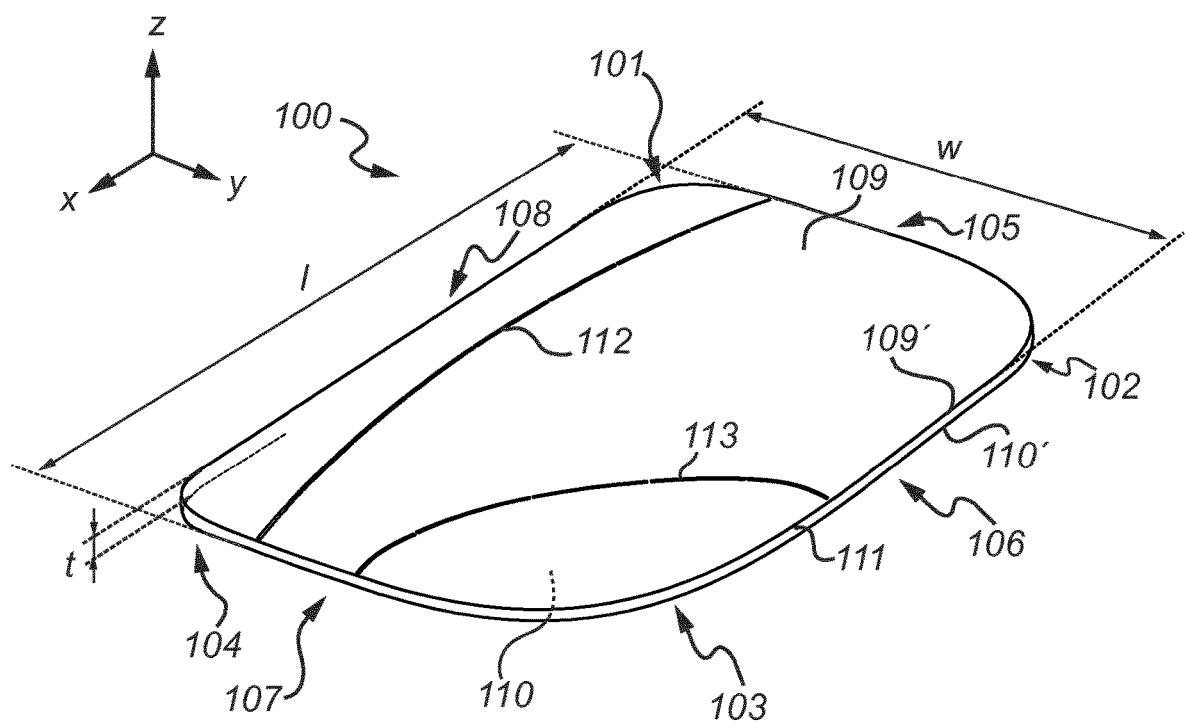
FIG. 12 shows a schematic perspective view of a substantially planar wound pad according to at least one exemplary embodiment of the present invention.

FIG. 12 illustrates a substantially planar wound pad 100 which is suitable as a wound filler. The wound pad 100 is formed as a one-piece wound pad and will be described with reference to a Cartesian coordinate system with three perpendicular axes labelled X, Y and Z, also depicted in FIG. 12. The main extension of the wound pad 100 is parallel to an X-Y plane. More specifically, the wound pad 100 has a length l in the X direction, a width w in the Y direction and a thickness t in the Z direction, and the thickness t is less, typically significantly less, than the width w which may be less than the length l.

The wound pad 100 has four corners 101, 102, 103, 104. In FIG. 12, all of the corners 101, 102, 103, 104 are rounded. Embodiments in which no corner is rounded, or only some of the corners are rounded, are conceivable. The projection on the X-Y plane of each of the corners 101, 102, 103, 104 has a curvature in the X-Y plane. At least one of these curvatures is different from the other curvatures. Some of the curvatures may thus be the same. Furthermore, one or more projections may have a constant curvature. All of, or some of, such constant curvatures may be different from each other.

The wound 100 pad also has four edge portions 105, 106, 107, 108 which connect two neighbouring corners 101, 102, 103, 104. As is illustrated in FIG. 12, the edge portions 105, 106, 107, 108 may be straight and may form two pairs of opposite edge portions, the edge portions of each pair being substantially parallel with each other and substantially perpendicular to the straight portions of the other pair. That is to say, the wound pad 100 may be substantially rectangular.

The wound pad 100 has a first main surface 109 which is flat and parallel with the X-Y plane. The circumference 109' of the first main surface 109' is straight between any two neighbouring corners 101, 102, 103, 104, i.e. the circumference 109' is straight by the edge portions 105, 106, 107, 108. By each of the corners 101, 102, 103 104, the circumference 109' has a curvature in the X-Y plane, the curvature by a specific corner being equal to the curvature of the projection in the X-Y plane of that corner. Hence, the first main surface 109 has a substantially rectangular shape.

The wound pad 100 further has a second main surface 110 which has the same shape as the first main surface 109. The first 109 and second 110 main surfaces are parallel with the X-Y plane and separated by the distance t in the Z direction. Like the circumference 109' of the first main surface 109', the circumference 110' of the second main surface 110 is straight by the edge portions 105, 106, 107, 108 and has a curvature in the X-Y plane by each of the corners 101, 102, 103 104, the curvature by a specific corner being equal to the curvature of the projection in the X-Y plane of that corner.

A circumferential surface 111, which has a smaller area than each of the first 109 and the second 110 main surfaces, extends in the Z direction between the first 109 and second 110 main surfaces. The circumferential surface 111 forms a closed path around the circumference of the wound pad 100, interconnecting the circumference 109' of the first main surface 109 with the circumference 110' of the second main surface 110. In FIG. 12, the circumferential surface 111 is straight in the Z direction and perpendicular to the X-Y plane. It should be noted that in other embodiments the circumferential surface 111 may have a curvature in the Z direction.

The wound pad 100 may have one or more main incomplete cuts 112, 113. The wound pad 100 in FIG. 12 has one main incomplete cut 113 which extends from one edge portion 106 to an adjacent edge portion 107 of the wound pad 100. The wound pad in FIG. 12 also has a main incomplete cut 112 extending from one edge portion 105 to an opposite edge portion 107.

The invention claimed is:

1. An article consisting of a wound pad for application in a wound, the wound pad consisting of an open-cell foam, wherein the open-cell foam comprises
   a main extension parallel to an X-Y plane of a Cartesian coordinate system with axes X, Y and Z; and
   a thickness in the Z direction of said Cartesian coordinate system;
   wherein the wound pad has a first corner, a second corner, a third corner, a fourth corner, a first perimeter edge, a second perimeter edge, a third perimeter edge, and a fourth perimeter edge that together define a shape and perimeter edge of the wound pad,
   wherein said first perimeter edge connects the first corner and the second corner,
   wherein the second perimeter edge connects to the second corner and the third corner,
   wherein the third perimeter edge connects the third corner and the fourth corner,
   wherein the fourth perimeter edge connects the fourth corner and the first corner,
   each corner being at least one of
      a) provided as a rounded corner, a projection of which on said X-Y plane has a radius of curvature, or
      b) removable, by manually separating a corner piece of the wound pad delineated by a corner incomplete cut so as to leave a rounded corner, a projection of which on said X-Y plane has a radius of curvature,
   wherein the projection on said X-Y plane of at least one rounded corner of a) or b) has a radius of curvature which differs from the radius of curvature of the projection on said X-Y plane of any of the other corners, wherein the wound pad only has two corner incomplete cuts being a first corner incomplete cut and a second corner incomplete cut, wherein in the first corner incomplete cut extends from the first perimeter edge to the third perimeter edge, wherein the second corner incomplete cut extends from the third perimeter edge to the fourth perimeter edge, wherein the second corner and the third corner are removable, by manually separating a piece of the wound pad delineated by the first corner incomplete cut, wherein the fourth corner is removable, by manually separating a corner piece of the wound pad delineated by the second corner incomplete cut, wherein the first and second corner incomplete cuts each comprises a plurality of cut segments and one or more connection regions, the one or more connection regions being respective uncut open-cell foam regions that extend continuously between adjacent cut segments, wherein each cut segment of the plurality of cut segments extends longitudinally in the X-Y plane, wherein each cut segment of the plurality of cut segments is separated from a neighbouring cut segment of the plurality of cut segments by one connection region of the one or more connection regions.

2. The article of claim 1, wherein the first corner, the second corner, the third corner, and the fourth corner are provided as a rounded corner.

3. The article of claim 1, wherein the first perimeter edge and the second perimeter edge are straight.

4. The article of claim 3, wherein the first perimeter edge and the third perimeter edge are opposite perimeter edges, wherein the second perimeter edge and the fourth perimeter edge are opposite perimeter edges, the perimeter edges of each pair of opposite perimeter edges being substantially parallel with each other and substantially perpendicular to the perimeter edges of the other pair of opposite perimeter edges.

5. The article of claim 1, wherein the radii of curvatures of at least two projections differ from the radii of curvature of the other projections.

6. The article of claim 5, wherein the radii of curvatures of the at least two projections differ from each other.

7. The article of claim 6, wherein the radii of curvatures of all projections differ from each other.

8. The article of claim 1, wherein the wound pad has a thickness,
further comprising at least one main incomplete cut, the at least one main incomplete cut extending through at least a portion of the thickness of the wound pad,
wherein the at least one main incomplete cut delineates at least two sections of the wound pad that can be manually separated from each other, and
wherein the wound pad is structurally intact.

9. The article of claim 1, wherein at least one of said projections has a constant radius of curvature.

10. The article of claim 1, wherein the open-cell foam comprises a polymer foam.

11. The article of claim 10, wherein the polymer foam comprises polyurethane foam, polyester foam, polyether foam, polyvinyl alcohol foam, or combinations thereof.

12. The article of claim 1, wherein the wound pad is suitable for use in negative pressure wound therapy.

13. A system for the treatment of wounds using negative pressure, comprising:
a negative pressure source for providing negative pressure to a wound,
the article according to claim 1,
a wound cover disposed over the wound pad, and
a conduit configured to transmit negative pressure from the negative pressure source to the wound cover.

14. A kit for negative pressure wound therapy, comprising the article according to claim 1 and at least one item selected from the group consisting of: a wound contact layer, a wound cover, and a wound interface device.

15. The article of claim 1, wherein the wound pad further comprises an incomplete cut extending from the second perimeter edge of the wound pad to the fourth perimeter edge of the wound pad.

16. The article of claim 1, wherein the first and second corner incomplete cuts are provided as a plurality of perforations.

* * * * *